(12) United States Patent
Belley et al.

(10) Patent No.: US 7,695,458 B2
(45) Date of Patent: *Apr. 13, 2010

(54) IV CATHETER WITH IN-LINE VALVE AND METHODS RELATED THERETO

(75) Inventors: Richard A. Belley, St. Louis, MO (US); Eugene F. Schrader, St. Louis, MO (US); Eugene E. Weilbacher, Chesterfield, MO (US); Richard Fiser, Kirkwood, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 248 days.

This patent is subject to a terminal disclaimer.

(21) Appl. No.: 11/546,752

(22) Filed: Oct. 11, 2006

(65) Prior Publication Data

US 2007/0083157 A1   Apr. 12, 2007

Related U.S. Application Data

(60) Provisional application No. 60/840,125, filed on Aug. 25, 2006, provisional application No. 60/726,026, filed on Oct. 11, 2005.

(51) Int. Cl.
*A61M 5/00* (2006.01)
*A61M 5/178* (2006.01)
*A61M 31/00* (2006.01)
*A61M 37/00* (2006.01)
(52) U.S. Cl. ............... 604/246; 604/167.01; 604/93.01
(58) Field of Classification Search ................ 604/246, 604/167.01–167.04
See application file for complete search history.

(56) References Cited

U.S. PATENT DOCUMENTS

| | | | |
|---|---|---|---|
| 4,143,853 A | 3/1979 | Abramson | |
| 4,424,833 A | 1/1984 | Spector et al. | |
| 4,430,081 A * | 2/1984 | Timmermans | 604/256 |
| 4,874,377 A | 10/1989 | Newgard et al. | |
| 4,895,346 A | 1/1990 | Steigerwald | |
| 4,909,798 A | 3/1990 | Fleischhacker et al. | |
| 4,917,668 A | 4/1990 | Haindl | |
| 4,960,412 A | 10/1990 | Fink | |
| 5,085,645 A | 2/1992 | Purdy et al. | |
| 5,215,538 A | 6/1993 | Larkin | |
| 5,242,393 A | 9/1993 | Brimhall et al. | |
| 5,322,518 A | 6/1994 | Schneider et al. | |
| 5,390,898 A | 2/1995 | Smedley et al. | |
| 5,535,771 A | 7/1996 | Purdy et al. | |
| 5,535,785 A | 7/1996 | Werge et al. | |
| 5,555,908 A | 9/1996 | Edwards et al. | |

(Continued)

*Primary Examiner*—Nicholas D Lucchesi
*Assistant Examiner*—Rebecca E Eisenberg
(74) *Attorney, Agent, or Firm*—Lisa E. Winsor, Esq.

(57) ABSTRACT

Featured is a vascular access device such as an IV catheter device including a housing, a tubular member, a seal member, a compression member, and a securing mechanism. The housing includes a proximal and distal portion and a chamber that extends between the proximal and distal housings. The tubular member is coupled to the housing distal portion so it is fluidly coupled to the chamber. The seal member is disposed within the chamber and the securing mechanism secures the seal member distal end to the housing proximal portion so the seal member is sealingly and compressibly retained between a chamber proximal end and the securing mechanism. Such a seal member also forms a septum, which is compressed by the compression member to prevent seepage upon removal of a stylet.

33 Claims, 26 Drawing Sheets

U.S. PATENT DOCUMENTS

| | | |
|---|---|---|
| 5,573,516 A | 11/1996 | Tyner |
| 5,676,346 A | 10/1997 | Leinsing |
| 5,738,144 A | 4/1998 | Rogers |
| 5,749,861 A | 5/1998 | Guala et al. |
| 5,776,113 A | 7/1998 | Daugherty et al. |
| 5,788,215 A | 8/1998 | Ryan |
| 5,806,551 A | 9/1998 | Meloul et al. |
| 5,806,831 A | 9/1998 | Paradis |
| 5,817,069 A | 10/1998 | Arnett |
| 5,954,313 A | 9/1999 | Ryan |
| 5,954,698 A | 9/1999 | Pike |
| 5,967,490 A | 10/1999 | Pike |
| 6,068,011 A | 5/2000 | Paradis |
| 6,068,617 A | 5/2000 | Richmond |
| 6,152,900 A | 11/2000 | Mayer |
| 6,158,458 A | 12/2000 | Ryan |
| 6,171,287 B1 | 1/2001 | Lynn et al. |
| 6,228,060 B1 | 5/2001 | Howell |
| 6,482,188 B1 | 11/2002 | Rogers et al. |
| 6,485,473 B1 | 11/2002 | Lynn |
| 6,699,221 B2 | 3/2004 | Vaillancourt |
| 6,740,063 B2 | 5/2004 | Lynn |
| 6,802,490 B2 | 10/2004 | Leinsing et al. |
| 2005/0203484 A1* | 9/2005 | Nowak ........................ 604/502 |

\* cited by examiner

Section A-A

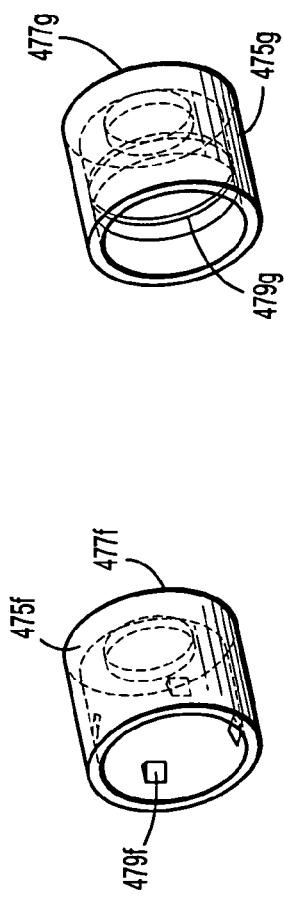
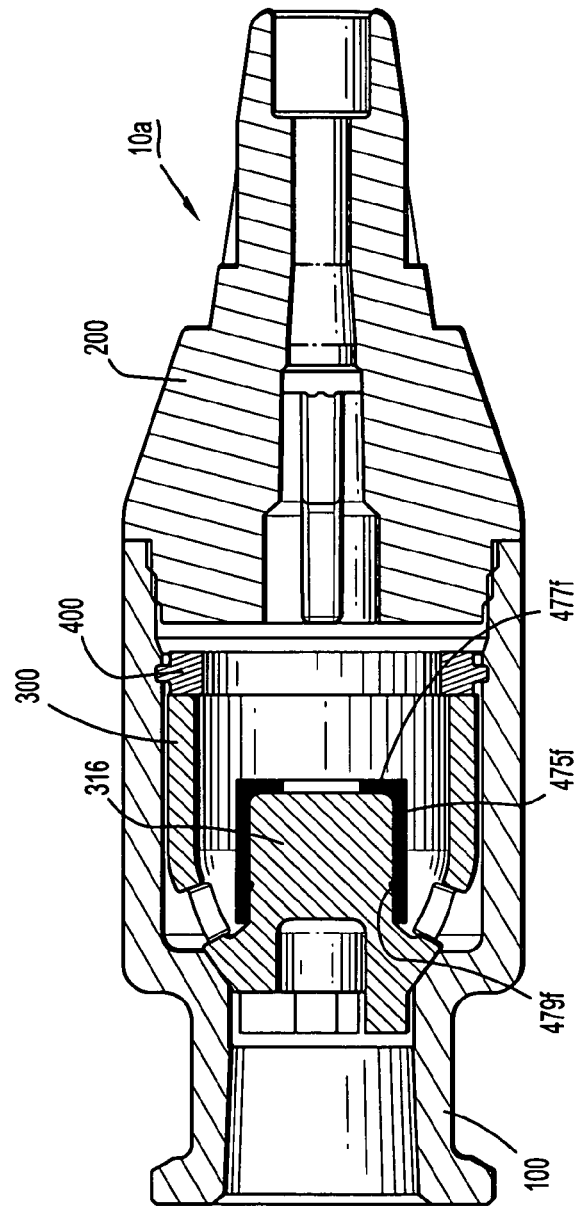
FIG. 10
FIG. 9A
FIG. 9B

IV CATHETER WITH IN-LINE VALVE AND METHODS RELATED THERETO

This application claims priority from U.S. Provisional Application Ser. No. 60/840,125, which was filed on Aug. 25, 2006, and from U.S. Provisional Application Ser. No. 60/726, 026, which was filed on Oct. 11, 2005. The entire contents of each are incorporated herein by reference.

FIELD OF INVENTION

The present invention generally relates to medical infusion or access devices such as intravenous (IV) catheters and more particularly to a vascular access device including a valve and more specifically to an over-the-needle IV catheter including an in-line valve and having a re-sealable septum compressed by a collar.

BACKGROUND OF THE INVENTION

Medical access devices, particularly infusion devices, over-the-needle catheters, other catheters and feeding tubes, are important tools for administration of fluids to patients. In the normal management of a catheter or other medical access device, after it is placed in a patient, it is often necessary to be able to add or withdraw fluids through the device. For example, in surgical procedures, it is a routine practice to place an intravenous catheter so that if it is necessary to medicate a patient during a procedure, the catheter already is in place. It also is common in post surgical situations or in other types of procedures to see medicaments be periodically administered and/or to see fluid sample(s) withdrawn. For example, an IV catheter may be placed in a patient when a stress test is being performed out of caution as well as when the testing process includes injecting a material into the vasculature for use in a subsequent imaging technique.

Over-the-needle catheters or over-the-needle IV catheters (such as that described in PCT Publication No. 2005-0096592) are used for peripheral intravenous entry into the vasculature of a patient. The disposable medical product is packaged as an assembly of a catheter adapter with its catheter and a needle and hub assembly that are arranged with respect to the catheter adapter so the needle passes through the catheter tube. The needle also extends a slight distance beyond the distal tip of the catheter tube so as to provide a sharpened point for penetration through the skin of the human or animal being catheterized.

After the catheter adapter with its catheter and a needle and hub assembly are inserted into the vasculature or blood vessel of the patient, blood flows due to the vascular blood pressure through the hollow needle and into the hub, sometimes referred to as flashback. Typically, the hub is arranged and configured so the medical personnel are provided a visual indicator of the blood flashback thereby indicating the tip of the needle and thus the distal end of the catheter tube is disposed in the blood vessel. One technique used is constructing the hub at least in part of a transparent material so that the blood flashback is visually apparent to the medical personnel.

According to one prior art technique, when flashback is observed, the practitioner or medical personnel places a finger against the skin of the human or animal and presses against the skin so as to compress the skin and the vessel there beneath and thereby occlude vessel blood flow proximal to the catheter tip. Such pressing against the vessel is supposed to thereby prevent the flow of blood back through the catheter tube, into the catheter adapter and out onto the patient, bedding, clothing and the like. Thereafter, the needle and hub as an assembly are removed from the catheter (e.g., the catheter hub is held by the clinician as the needle is being pulled).

While efforts are undertaken in this approach to prevent blood flow back through the catheter tube, such efforts are typically not completely effective and some blood flows onto the patient, bedding, clothing and the like. As such, this approach is of some concern because of the possibility of the spread of communicable diseases, particularly those such as HIV and Hepatitis. As such, a technique has been developed to minimize exposure to blood whereby the needle and hub assembly is removed from the catheter and adapter assembly without having to use the hand which positions the patient's arm to also press and stop blood flow. In this other technique, a mechanism is provided that automatically isolates the blood vessel from the open end of the catheter hub thereby preventing blood loss when the needle and hub assembly is and has been separated from the catheter and adapter assembly.

There is described in U.S. Pat. No. ("USP") 5,085,645 (Purdy et al.), an over-the-needle type of catheter having an adapter including a valve between and in a passage defined in distal and proximal parts of a housing. The described adapter is arranged so as to be an integral part of the catheter hub. In U.S. Pat. No. 5,535,771 (Purdy et al.), there is described a valved adapter for an infusion device.

Others have indicated (see the Background section of U.S. Pat. No. 5,967,490; Pike) that the device described in U.S. Pat. No. 5,085,645 includes an elongate resilient valve (i.e., its length is greater than its width) having a large internal cavity. Such an elongate valve is believed to be unstable and tends to deflect or travel in a non-linear manner during use, thus creating an unreliable seal, possibly resulting in leakage. Valve leakage can create significant discomfort for the patient and increased risk of infection, along with increased risk of exposure to blood borne pathogens for healthcare workers.

Further, the internal cavity of the prior art device has a tendency to collapse during use as a result of the blood pressure of the patient. This could unseat the valve and produce leakage. Also, the internal cavity results in significant "dead" space in the flow path, in which blood or liquid can get trapped. Such trapped fluids can pose a risk of infection and/or thrombosis to the patient. In addition to the above, an elongate valve results in a longer catheter, which is harder for healthcare workers to use while being more expensive to fabricate.

There is described in U.S. Pat. No. 5,967,698 (Pike) a catheter hub including a housing having a connection end defining a first fluid passageway and a catheter end defining a second fluid passageway. The housing includes a plurality of hub walls arranged in a geometric configuration and which hub walls define a valve chamber. The catheter hub further includes a valve positioned in the valve chamber for controlling fluid flow through the chamber between the first and second fluid passageways and an actuator for actuating the valve. The valve is described as being of a substantially cylindrical configuration and is made of a resilient material. In use, a luer projection contacts the actuator, which in turn causes the valve to move axially within the housing thereby opening the valve. The actuator includes an annular flange that is received in a recess in the valve so as to provide structural support to the valve at the actuator end thereof.

There is described in U.S. Pat. No. 5,954,698 (Pike) a catheter apparatus having a needle protector attached to a catheter hub, which needle protector includes a needle. The catheter hub defines a valve chamber, and a valve is positioned in the chamber for controlling fluid flow through the chamber. The valve and catheter hub illustrated therein is the same as that described above for U.S. Pat. No. 5,967,698.

There is described in U.S. Pat. No. 5,817,069 (Arnett) a valve assembly having a body, an end cap, a resilient septum, and an actuator. The body forms a plurality of fluid recesses and the end cap defines a plurality of projections that form channels. The septum is positioned between the body and the end cap. The actuator device is positioned adjacent to the septum so the septum causes the actuator device to be put into sealing engagement with a shoulder defined in the body when in the closed position. When the actuator device is manipulated so the valve assembly is put into the open condition, the actuator device is moved against the septum thereby also moving the actuator device away from the shoulder in the body thereby allowing fluid to pass through the body, actuator, and end cap. The actuator device also is configured with fluid passageways so the fluid flows through the actuator.

There is described in U.S. Pat. No. 5,242,393 (Brimhall et al.) an infusion site for infusing fluids into a patient. The infusion site includes a housing that supports a pre-slit resealable septum, which is held in radial compression in the housing. The housing also accommodates a valve, which is held in tension in the housing and is opened by the insertion of a cannula into the septum. The valve is closed when the cannula is withdrawn. The septum and valve are linked by an elastic member that interacts with the cannula to open and close the valve.

There is described in U.S. Pat. No. 5,788,215 (Ryan) a medical intravenous administration connector including a first coupling member having a female luer, a valve member having a substantially rigid stem and a substantially resilient body with a sealing surface, and a second coupling member having a fluid coupling extending from one end and an internal valve member support. The coupling members are structured to couple to each other with the valve member being biased to a closed position. When assembled, the valve stem extends into the female luer, and the valve body biases the sealing surface against an annular ring in the first coupling member thereby blocking fluid communication. Preferably, vanes are provided in the second coupling member on which the resilient body of the valve sits, with the vanes acting as a centering mechanism for the valve. The valve may be opened for fluid flow through the assembly by coupling a male luer to the female luer of the assembly, or by pressure actuation. Several valve members are disclosed and several structures for mating the first and second coupling members are disclosed.

There is described in U.S. Pat. No. 5,215,538 (Larkin) an in-line valve for a medical tubing set that has a tubular member characterized by an internal annular valve seat and a generally circular rubber-like valve member disposed transversely of the tubular member with its edges fixed relative thereto and with a central portion thereof tensioned into seating engagement against the annular valve seat to normally close the in-line valve. Valve member elements are engageable by a connector as same is assembled to the tubular member to move the valve member off of the valve seat to automatically open the in-line valve.

Because there is a large demand for using such IV catheters in surgical and non-surgical environments, it is common to store large number of such IV catheters for ready access for such use or so such IV catheters can be readily shipped to the user. Consequently, the effects of such storage (e.g., cold flow) are a consideration in the design of IV catheters.

There is described in U.S. Pat. No. 6,228,060 (Howell) a blood seal having a spring-biased septum. The spring-biased septum includes an elastic plug with a groove. A biasing element is disposed about the plug within the groove.

There is described in U.S. Pat. No. 5,573,516 (Tyner) a needleless connector having a two-part housing with an inlet, an outlet, and a conical chamber therebetween. The conical chamber compressibly receives a resilient conical valve head. The conical valve head includes a stationary base, and a tip portion movably extending into the inlet. The conical valve head is concentrically positioned against the valve seat to form a seal. When the male fitting of a syringe, or some other device, is inserted into the inlet, it pushes a tip portion of the resilient valve head inwardly, so that the valve head is deformed away from the valve seat to break the seal.

It thus would be desirable to provide a new vascular access device such as an IV catheter device including an in-line valve for controlling the flow of fluid in either direction through the vascular access/IV catheter device and methods related thereto. It would be particularly desirable to provide such a device in which the seal member of the valve is sealingly disposed and retained only within a proximal portion of the device. It would be further desirable to provide a valve member suited for long-term storage with the needle or cannula inserted therethrough. It also would be desirable to provide such a device that is less complex in structure, manufacture and operation as compared to prior art devices. Also it would be desirable that such methods would not require highly skilled users to utilize the catheter device.

SUMMARY OF THE INVENTION

The present invention features a vascular access device such as an IV catheter device as well methods for making and using such vascular access devices/IV catheter devices. More particularly, such a vascular access device includes a housing including a proximal portion, a distal portion and a chamber therein extending between the proximal and distal portions. A tubular member is coupled to the distal portion and defines a lumen therein that is fluidly coupled to the chamber. A seal member is disposed within the chamber, such that the seal member is sealingly engaged to a region of the proximal portion and wherein the seal member includes a septum configured to removably receive an introducer needle. A compression member is coupled to the seal member for providing a compression force to assist re-sealing during and after withdrawal of the introducer needle from the septum.

In another embodiment, a vascular device includes a housing formed at least by a housing proximal portion and a housing distal portion that establishes a chamber therein extending between the proximal and distal housings. Such a vascular access device also includes a seal member and a securing mechanism. The seal member is disposed within the chamber and has a septum, a distal end, a proximal end, and a sealing portion, which sealingly engages with at least a portion of the junction. The securing mechanism secures the seal member distal end with the region of the proximal portion. Also, the seal member distal end is proximal to and not in contact with the housing distal portion, such that the seal member is sealingly and compressibly retained between the proximal end of the chamber and the securing mechanism. The housing proximal portion may include a distal reduced-diameter portion and a widened portion and the chamber may have a proximal end at a junction of the reduced-diameter portion and the widened portion. Also, the seal member sealing portion sealingly engages with at least a portion of the junction.

In further embodiments/aspects, the present invention features an over-the-needle IV catheter device through which an object, such as an introducer needle, an insertion needle, an insertion cannula or the like, is removably passed therethrough. Such an IV catheter device includes a housing, a tubular member and a seal member, and a securing mechanism. The housing includes a proximal portion, a distal portion and a chamber therein extending between the proximal and distal housings. The tubular member is coupled to the housing distal portion so a lumen thereof is fluidly coupled to the chamber. The seal member is disposed within the chamber and the securing mechanism secures the seal member distal end to the housing proximal portion such that the seal member is sealingly and compressibly retained between a proximal end of the chamber and the securing mechanism. Such a seal member also is constituted and arranged so a portion thereof, a sealing portion, moves axially responsive to an axial force applied to the proximal end. As described further herein, the sealing portions can be thus displaced from the chamber proximal end such that the sealing portion is no longer in sealing engagement with the chamber proximal end.

The seal member also is configured so as to include a septum in which is removably received an introducer needle. In particular embodiments, a portion of the seal member proximal end includes a sealing portion for sealing engagement with at least a portion of the chamber proximal end and the seal member is configured so the septum lies in the same general plane as the sealing portion. In other embodiments, the seal member is configured so that the septum is spaced from the proximal end or the septum is spaced from the sealing portion(s). More specifically, the septum is spaced in a distal direction from the proximal end or the sealing portion(s).

In more particular embodiments, the seal member further includes one or more axially extending walls that extend from the proximal end into the seal member inner cavity. Also, the septum is secured to a common end of the one or more walls so as to form a pocket extending from the proximal end to the septum.

In further embodiments, the seal member further includes a collar portion comprising one or more axially extending walls. Such a collar portion is secured to a bottom surface of the septum so that the one or more axially extending walls extend into the seal member inner cavity. In exemplary embodiments, the collar portion comprises an axially extending annular structure that more specifically forms an integral structure with the septum.

In further embodiments, the seal member proximal end includes a plurality of raised sections, a plurality of channels and a centrally located chamber. The plurality of channels are arranged so as to extend between an outside surface of the raised sections and the centrally located chamber.

In particular embodiments, the securing mechanism is a ring member that is secured to the housing proximal portion using any of a number of techniques known to those skilled in the art. Also, the ring member is secured to the housing proximal portion so that the seal member is engaged between a surface (a top surface) of the ring member and sealingly and compressibly engaged with the proximal end of the chamber. In more particular embodiments, the ring member is mechanically secured to the housing proximal portion.

In further embodiments, an inner surface of a portion of the chamber that is in the housing proximal portion is configured so as to include a depression that is located a preset distance from the chamber proximal end. The ring member is mechanically secured within the depression to the housing proximal portion. Such mechanically securing includes one of an adhesive, snap-fit, press-fit, interference fit, welding or other types/forms of known mechanical connections.

In an illustrative exemplary embodiment, the depression comprises a groove provided (e.g., machined, formed, cast, molded) in the inner surface of the chamber portion in the housing proximal portion that is located a preset distance from the chamber proximal end. After the seal member is inserted into the proximal housing, the ring member is manipulated so a portion of the ring member is disposed within the groove thereby forming a mechanical connection between the proximal housing and the ring member. More specifically, the groove is arranged so as to have a width that restricts axial or side-to-side movement of the ring member within the groove.

In another illustrative exemplary embodiment, the depression comprises a combination of a lip or shoulder and a rib or step structure in the inner surface. The lip is provided (e.g., machined, formed, cast, molded) in the inner surface of the chamber portion in the housing proximal portion that is located a preset distance from the chamber proximal end. The rib is displaced axially from the lip and extends circumferentially about the inner surface and radially outwardly from the inner surface (i.e., towards a long axis of the distal housing). After the seal member is inserted into the proximal housing, the ring member is manipulated so a portion of the ring member is disposed between the lip and the rib thereby forming a mechanical connection between the proximal housing and the ring member. In further embodiments, the lip and rib are arranged so the spacing therebetween is sufficient to restrict axial or side-to-side movement of the ring member when it is disposed between the lip and rib.

In more particular illustrative embodiments, the rib is configured so as to have a distal side surface extending in a distal direction, the distal side surface being a sloped surface. In further embodiments, the rib includes a proximal side surface having a first portion that is substantially parallel to the vertical surface of the lip and having a second portion that slopes upwardly and distally from the first portion to the top of the rib. The sloped distal side surface among other things facilitates axial movement of the ring member during the insertion process.

In yet further illustrative embodiments, the depression comprises a lip or shoulder that is provided (e.g., machined, formed, cast, molded) in the inner surface of the chamber portion in the housing proximal portion that is located a preset distance from the chamber proximal end. After the seal member is inserted into the proximal housing, the ring member is manipulated so as to be adjacent to or abut the lip. In one embodiment, the inner diameter of the region of the inner surface proximal the lip is arranged so that there is an interference fit between the ring member and the inner surface thereby mechanically engaging the ring member with the inner surface. Alternatively, any of a number of securing techniques known to those skilled in the art is used to mechanically secure the ring member to the proximal housing so as to be adjacent to or abutting the lip.

In further embodiments, the distal portion includes a plurality of axially extending fins that extend inwardly from an inner surface of a portion of the inner chamber disposed within the distal portion, the fins being arranged so as to create any of a number of structural arrangements known to those skilled in the art and appropriate for the intended use. Such a structural arrangement being such as to form a physical barrier or stop to limit axial movement of the seal member in response to abnormally high pressure flow fluid conditions while maintaining adequate flow area for passage of fluid through the IV catheter in either distal or proximal directions. Such an arrangement also should allow the object (e.g., introducer needle, insertion cannula or the like) to pass through the IV catheter in the intended manner. More particularly, the axially extending fins are arranged so they do not contact the securing mechanism (e.g., the ring member). Still more particularly, the fins are arranged so they clear the seal member at all times during normal on/off operation. In exemplary embodiments, the plurality of axially extending fins extend radially inwardly from the inner surface so as to form a stop structure that is opposite to the seal member septum and so as to provide a centrally located axially extending open region through which the introducer needle passes as well as an open flow area for the passage of fluid. In other exemplary embodiments, the plurality of axially extending fins extend inwardly from the inner surface in a non-radial fashion so as to form a stop structure that is to the seal member septum and so as to provide a centrally located axially extending open region through which the introducer needle passes.

In yet other exemplary embodiments, the stop structure comprises a grate like structure (e.g., a structure composed of intersecting members that extend chord like across the inner surface of the distal housing). Such intersecting members also are arranged so as to form a stop structure that is opposite to the seal member septum and so as to provide a centrally located open region through which the introducer needle passes as well as providing an open flow area for the passage of fluid.

The present invention also features such an over-the-needle catheter device in combination with an introducer needle. This shall not be considered limiting as the IV catheter of the present invention is adaptable for use with any of a number of medical devices or catheters which embody an in-line valve or valve. In particular, the IV catheter of the present invention is adaptable for use with any of a number of medical devices or catheters in which an object is removably passed through the catheter. Also featured are device kits including an IV catheter of the present invention, such as for example, a device including an over-the-needle catheter device embodying an in-line IV catheter of the present invention and an introducer needle. According to these aspects of the present invention, the introducer needle or object extends axially within the housing and so as to sealingly pass through the seal member septum of the catheter device.

As well as featuring methods for using such devices, the present invention also features a method for making such in-line valve over-the-needle IV catheter devices. Such methods include the steps of providing a proximal housing having an internal cavity, a proximal end and a distal end, where the internal cavity includes a proximal end and providing a distal housing having an internal cavity, proximal and distal end. Such methods also include securing a tubular member to the distal housing such that a lumen of the tubular member is fluidly coupled to the distal housing internal cavity and disposing a seal member having a proximal end and a distal end, where the proximal end includes a sealing portion within the proximal housing internal cavity. Such methods further include securing the seal member distal end to the proximal housing such that the seal member is sealingly and compressibly retained between the proximal end of the proximal housing inner cavity and ring member. The seal member is secured to the proximal housing and the proximal and distal housings are secured together.

The present invention also features an in-line valve connector, sometimes also referred to generally as a needleless connector for use in fluid connection with medical applications such as with intravenous lines. Such a needleless connector, according to the present invention, includes a housing, a seal member, and a securing mechanism. The housing includes a proximal portion, a distal portion and a chamber therein extending between the proximal and distal portions. The housing distal portion is configured so as to include a fluid connection that is fluidly coupled to the chamber. The housing proximal portion also is configured so as to include a fluid connection that is fluidly coupled to the chamber. These fluid connections can embody any of a number of connection techniques known to those skilled in the arts, such as for example, luer type connections.

Another embodiment of the subject invention features an in-line valve IV catheter device including a housing, a tubular member, a seal member, a septum collar, and a securing mechanism. The housing includes a proximal portion, a distal portion and a chamber therein extending between the proximal and distal housings. The tubular member is coupled to the housing distal portion and defines a lumen therein that is fluidly coupled to the chamber. The seal member is disposed within the chamber and the securing mechanism (e.g., a ring member) secures the seal member distal end to the housing proximal portion such that the seal member is sealingly and compressibly retained between a proximal end of the chamber and the securing mechanism. More particularly, the seal member includes a septum and is configured so the septum is spaced from the seal member distal end through which septum is passed an introducer needle/cannula to facilitate insertion of the tubular member into the vasculature of a mammal.

The septum collar is disposed about the septum and is configured so that when the septum is so disposed, the septum collar radially compresses the septum. In this way, when an introducer needle/cannula is removed from the septum, the radial compression facilitates and urges the material comprising the septum to seal the opening in the septum in which the introducer needle/cannula was located. In one embodiment, the collar is arranged so as to be disposed about a portion of the circumference of the septum. The portion is sufficient to cause such radial compression of the septum by the septum collar.

In another embodiment, the collar is arranged so as to be disposed about the entire circumference of the septum. Also, while in illustrative embodiments, the septum collar is configured so as to form a band of material about the septum, this shall not be a limitation, as it is contemplated and thus within the scope of the present invention for the septum collar to comprise any of a number of arrangements that can cause such radial compression. For example, in illustrative embodiments, the septum collar comprises a plurality of arcuate and axially extending segments that are interconnected to each other to form a collar or ring like structure about the septum.

In further embodiments, the seal member includes a plurality of through-apertures extending between an inner cavity and an outside surface of the seal member, and the seal member is arranged in the proximal housing so that the seal member inner cavity is fluidly coupled to a portion of the chamber disposed in the housing distal portion. In yet further embodiments, the seal member further includes a proximal end, a portion of which includes a sealing portion for sealing engagement with at least a portion of the chamber proximal end, and the proximal housing further includes a through opening that is fluidly coupled to the proximal end of the chamber, which opening is selectively fluidly coupled to the seal member inner cavity by the seal member sealing portion.

Another embodiment is directed to a vascular access device including a housing formed at least by a housing proximal portion and a housing distal portion which establish a chamber therein extending between the proximal and distal housings, the housing proximal portion having a distal reduced-diameter portion and a widened portion, the chamber having a proximal end at a junction of the reduced-diameter portion and the widened portion. A seal member, disposed within the chamber, has a septum and a sealing portion which sealingly engages with at least a portion of the junction. In further embodiments, the seal member is configured so the septum is spaced from the sealing portion and the vascular access device includes a septum collar that surrounds and radially compresses the septum. An introducer needle/cannula may pass through the septum such that the septum reseals upon removal of the introducer. Preferably, the septum has a preformed slit for the introducer needle/cannula.

Still another embodiment is directed to an in-line IV catheter device including a housing defining an interior having a proximal portion and a distal portion. An elongated cannula removably extends through the interior and defines an axis. A seal member is within the proximal portion for sealing to the proximal housing and thereby preventing fluid flow in a proximal and distal direction through the in-line valve IV catheter device. The seal member has sidewalls that extend along the axis forming a proximal cavity and terminating distally in a septum. A compression collar at least partially surrounds the septum to provide a radially compressive force on the septum. When fluid flow in either direction through the in-line valve IV device is desired, the seal member is displaced from the proximal portion to establish an open fluid flow path within the proximal portion in the proximal and distal direction. In a further embodiment, the seal member is constructed of a generally resilient material and includes raised sections extending proximally from the sidewalls to form at least one channel fluidly coupled with the interior. Preferably, the septum has a preformed slit for the cannula.

Other aspects and embodiments of the invention are discussed below.

DEFINITIONS

The instant/present invention is most clearly understood with reference to the following definitions:

The term "co-planar septum" shall be understood to mean a septum that is located essentially on the same axial plane as the seat area.

The term "proximal" shall be understood to mean or refer to a location on the device object or part being discussed which is closest to the medical personnel and farthest from the patient in connection with whom the device is used when the device is used in its normal operation.

The term "distal" shall be understood to mean or refer to a location on the device, object or part being discussed which is farthest from the medical personnel and closest to the patient in connection with whom the device is used when the device is used in its normal operation.

The term "medical personnel" shall be understood to be generally inclusive of clinicians, surgeons, medical technicians, lab technicians, nurses and the like.

The term "patient" shall be understood to include both human and animals and also shall be inclusive of humans or animals that are undergoing medical procedures including but not limited to surgical procedures and diagnostic procedures, medical treatments and/or other techniques/procedures/treatments performed in hospitals clinics, doctor's offices, diagnostic facilities/laboratories or the like.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views whenever possible and wherein:

FIG. 9A is a perspective view of another compression member for use in an IV catheter;

FIG. 9B is an assembled, cross-sectional, perspective view of an IV catheter with the compression member of FIG. 9A in place;

FIG. 10 is a perspective view of yet another compression member for use in an IV catheter;

DESCRIPTION OF PREFERRED EMBODIMENTS

Figure 1:
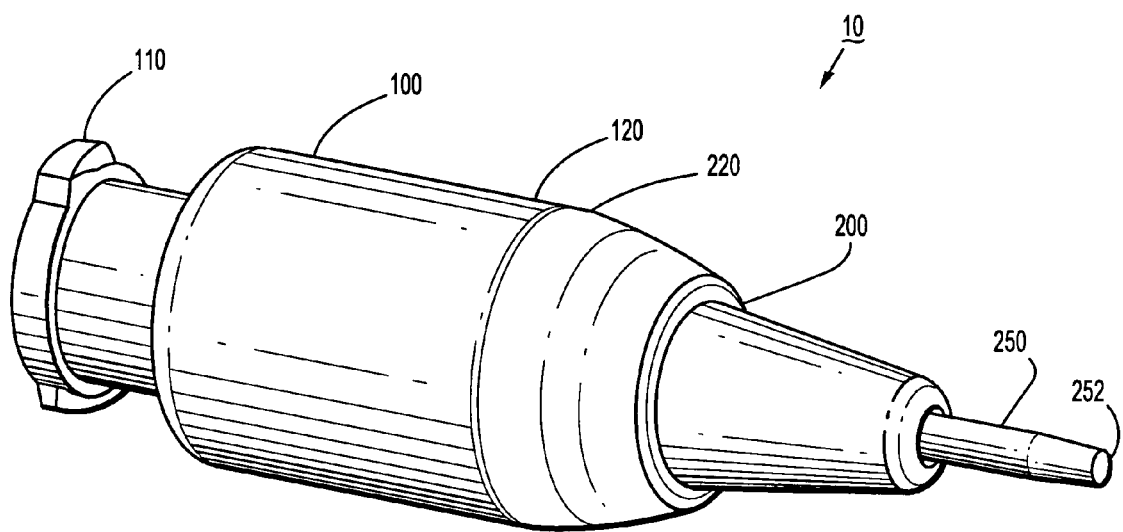
FIG. 1 is an axonometric view of an in-line valve IV catheter.

Referring now to the various figures of the drawings wherein like reference characters refer to like parts, there is shown in FIG. 1 an axonometric view of an in-line valve IV catheter assembly 10, which is a type of vascular access device, that is of the catheter-over-stylet/sharp/cannula type of IV catheter (Note: The catheter length is represented shorter than usual for simplicity). The stylet/sharp/cannula 20 (e.g., see FIGS. 2A,I) is inserted through the IV catheter assembly 10 or IV catheter so that the piercing end of the stylet/sharp/cannula 20 extends out of the open end 252 of the catheter tubular member 250. In this way, and as known to those skilled in the art, a user inserts the piercing end of the stylet/sharp/cannula 20 through the skin and subcutaneous tissue of the body so that the open end 252 of the tubular member 250 of the IV catheter assembly 10 is disposed within the blood vessel (e.g., vein or artery) of the patient.

Referring now to FIG. 1, the in-line valve IV catheter assembly 10 includes a proximal housing 100 with a mating end 120 and a distal housing 200 with a mating end 220 that are secured to each other so as to form an integral unit and so as to form a pressure boundary. Although not shown in FIG. 1 (e.g., see FIG. 2A) such an in-line valve IV catheter assembly 10 also includes a seal member 300 and a locking ring member 400 that sealingly secures the seal member within the proximal housing (i.e., in the sealing configuration). When in the valve closed configuration, at least a portion of the seal member 300 sealingly engages some inner surfaces of the proximal housing 100 thereby preventing fluid flowing in either proximal or distal directions through the in-line valve IV catheter assembly 10. When fluid flow in either direction through the in-line valve IV catheter 10 is desired (i.e., the valve open configuration), the seal member 300 is manipulated so at least a portion of the seal member in sealing engagement with inner surfaces of the proximal housing 100 is displaced from these inner surfaces. As is more particularly described herein, such displacement establishes an open fluid flow path within the proximal housing in either the proximal or distal directions.

A coupling end 110 of the proximal housing 100 is generally configured so as to be removably coupled to an external device (not shown) such as syringe, IV drip, IV pump or the like so as to allow a fluid sample(s) to be removed from the patient via the IV catheter assembly 10 or so fluid can be injected into the patient via the IV catheter assembly. In particular illustrative embodiments, the proximal housing coupling end 110 is configured to form a luer lock type end connection as is known to those skilled in the art, although the end connection can be any of a number of connections known or hereinafter developed that is appropriate for the intended use. It also should be recognized that such fluid being injected also can contain or be adapted or be adjusted so as to include any of a number of medicaments, drugs, antibiotics, pain medication and the like as is known to those skilled in the art for treatment and/or diagnosis.

Now referring to FIGS. 2A-I, there are shown various views of an in-line valve IV catheter assembly 10a according to one aspect and components or features thereof. Such an in-line valve IV catheter assembly 10a includes a proximal housing 100, a distal housing 200, a seal member 300, a locking ring member 400 and a compression member or collar 475. Throughout the present disclosure, the structure identified by reference character 475 may be interchangeably referred to as either "the compression member" or "the collar." Reference shall be made to the foregoing discussion of the proximal and distal housings 100, 200 of FIG. 1 for further details of the proximal and distal housings 100, 200 not otherwise described below.

Figure 2A:
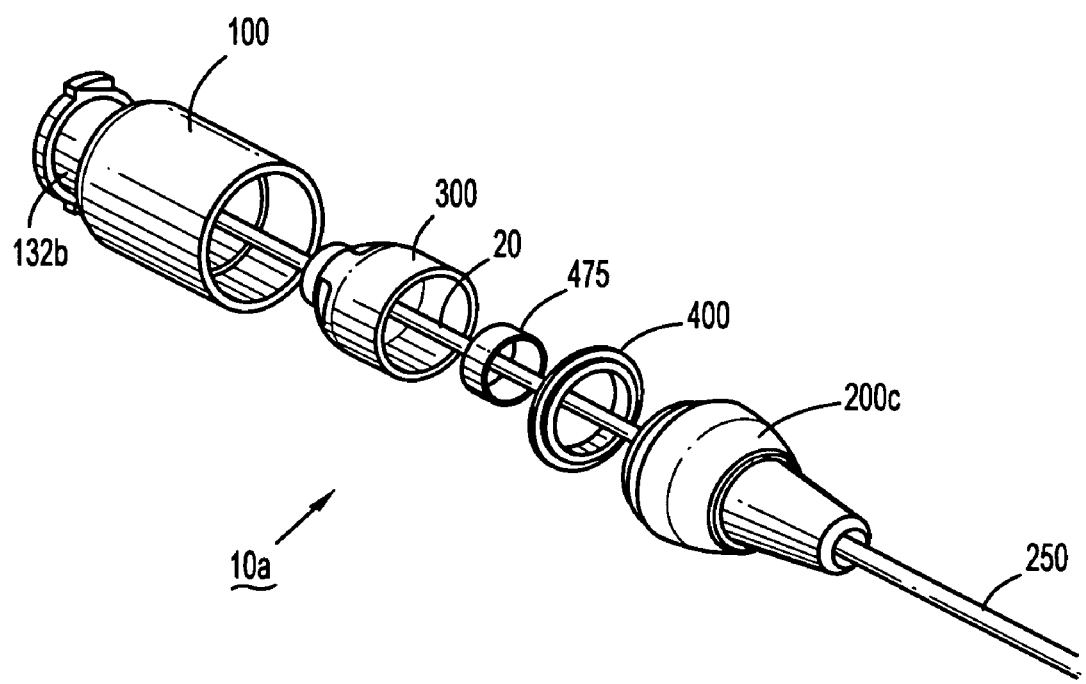
FIG. 2A is an exploded view of another aspect of an in-line valve IV catheter having a seal member with a septum having a compression collar.
Figure 2B:
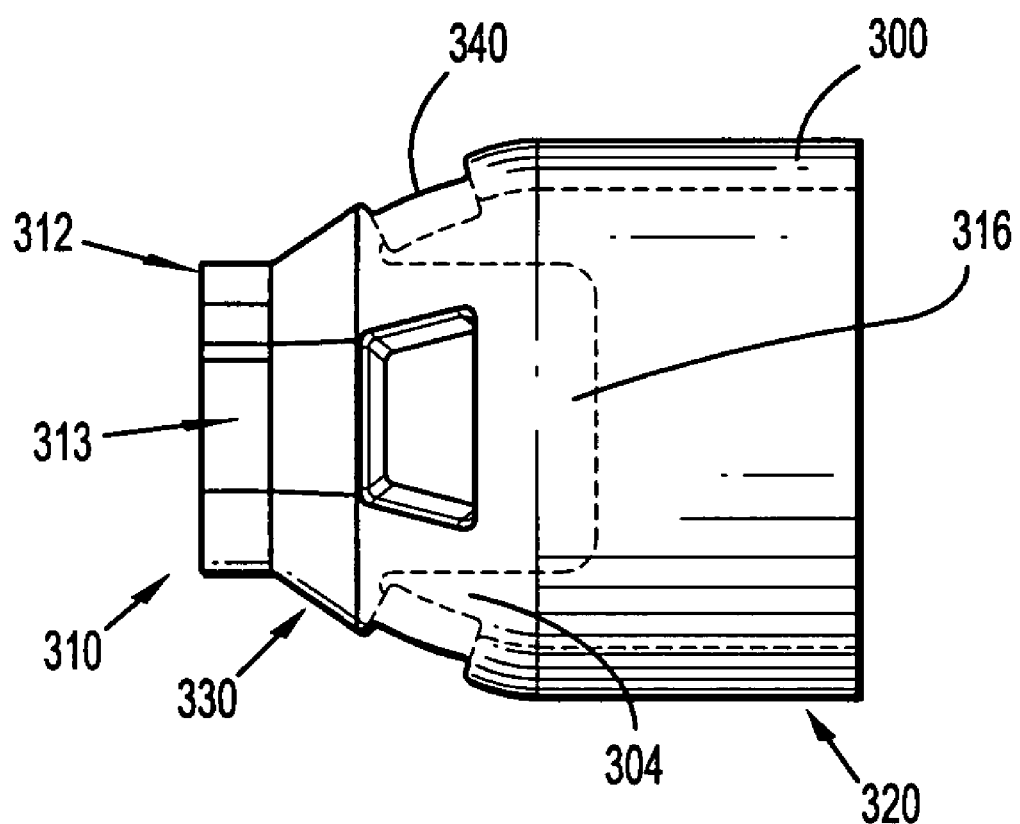
FIG. 2B is a side view of a seal member with a remote septum for use in the IV catheter of FIG. 2A.
Figure 2C:
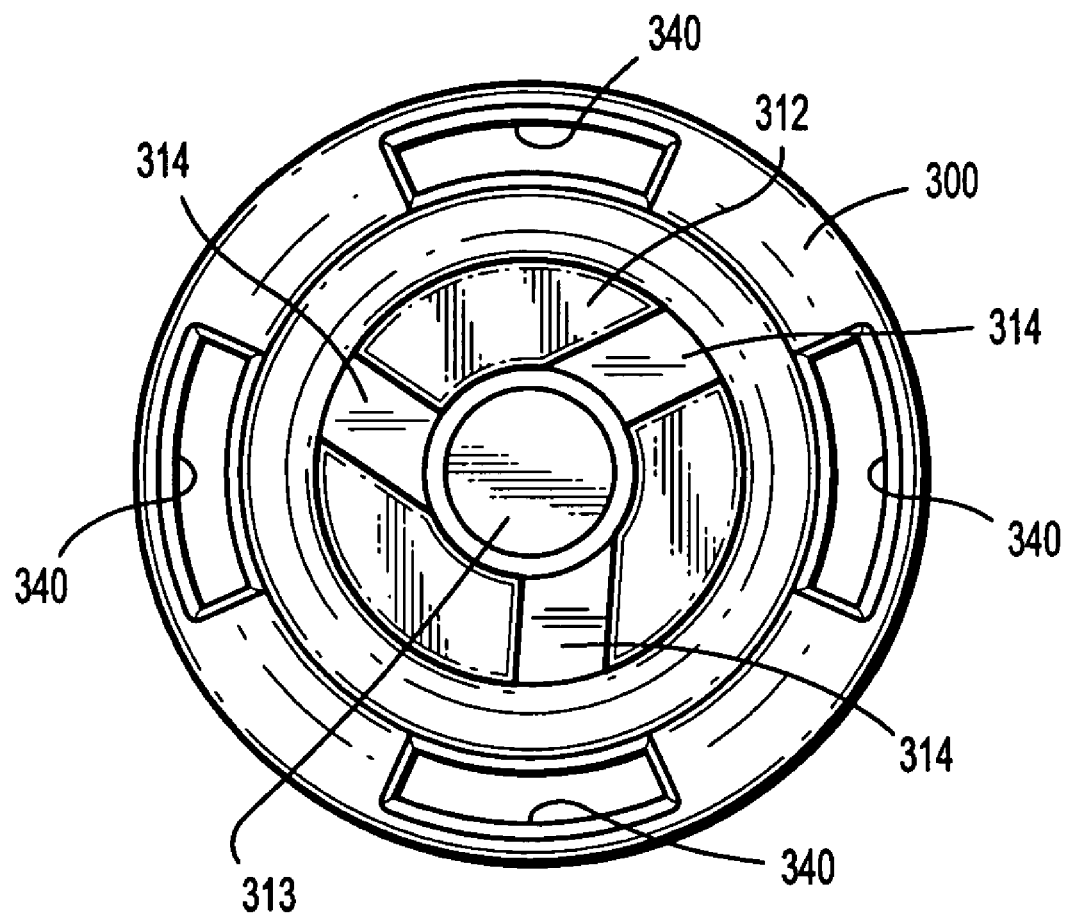
FIG. 2C is a proximal end view of a seal member with a remote septum for use in the IV catheter of FIG. 2A.
Figure 2D:
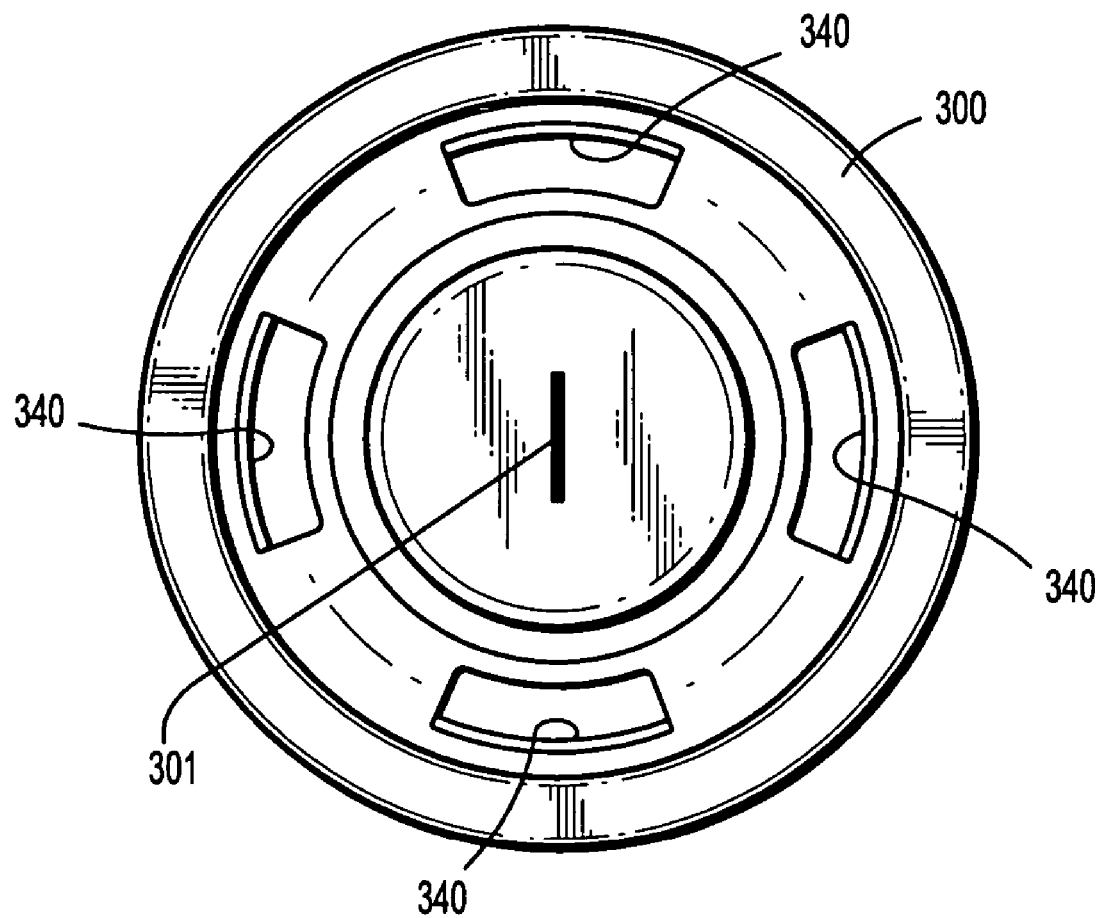
FIG. 2D is a distal end view of a seal member with a remote septum for use in the IV catheter of FIG. 2A.
Figure 2E:
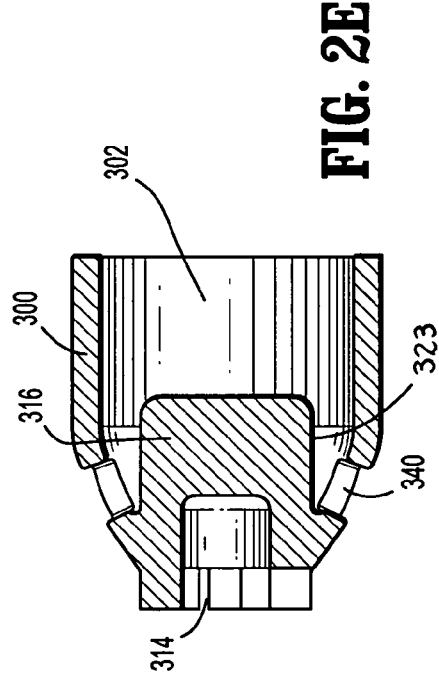
FIG. 2E is a cross-sectional view of a seal member with a remote septum for use in the IV catheter of FIG. 2A.
Figure 2H:
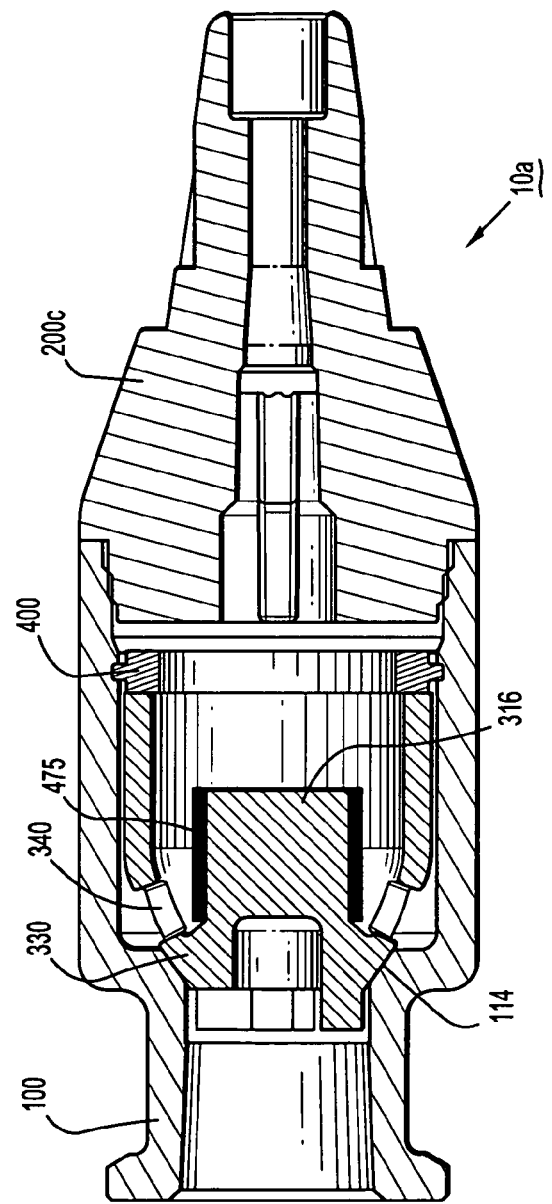
FIG. 2H is an assembled, cross-sectional, perspective view of the IV catheter of FIG. 2A without the stylet in place.
Figure 2F:
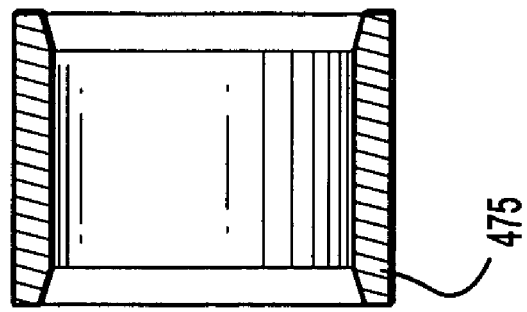
FIG. 2F is a side view of a compression collar for use in the IV catheter of FIG. 2A.
Figure 2G:
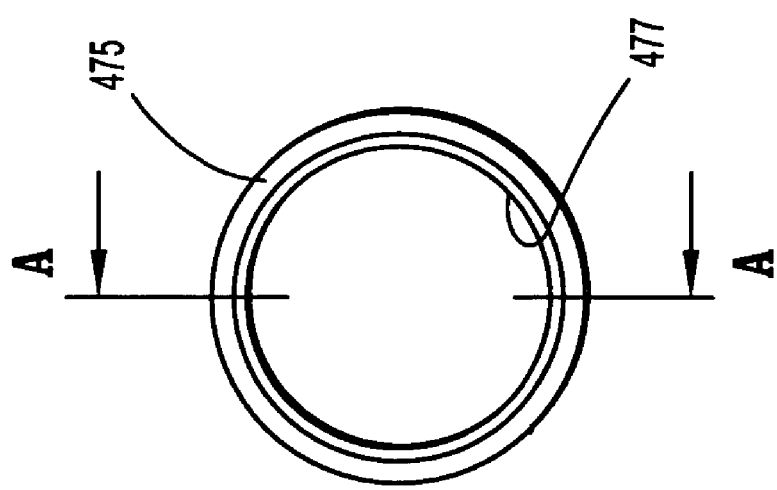
FIG. 2G is an end view of a compression collar for use in the IV catheter of FIG. 2A.

As more particularly illustrated in FIGS. 2H,I, the proximal and distal housings 100, 200 are joined to each other to form a pressure boundary body of the IV catheter assembly 10a. It is noted that no part of the distal housing 200 acts on or applies a force to the seal member 300 so as to thereby cause the seal member to be put into sealing engagement with some inner surfaces of the proximal housing 100. Rather, the sealing engagement results from the compression of the seal member 300 by the locking ring member 400 when the ring member is secured to the proximal housing 100 at a predetermined location within the proximal housing 100.

In exemplary, illustrative embodiments, the seal member 300 is a bell shaped member (e.g., see FIG. 2B). Other shapes, however, can be utilized and thus are contemplated which other shapes are generally characterized as being capable of exhibiting or achieving the herein described mechanical and sealing characteristics for the seal member 300. The seal member 300 also is constructed of a generally resilient material (e.g., an elastomeric material) that allows at least a portion of the seal member to be compressed and/or axially moved along its long or longitudinal axis as herein further described. It should be recognized the foregoing shall not be construed as being limiting as it is contemplated that the seal member can be constituted of materials having different characteristics including different structural or flexibility characteristics.

Such a seal member 300 includes a proximal end 310, a distal portion 320, a sealing portion 330, an inner cavity 302 (FIG. 2E) and one or more of windows 340 or through-apertures. In more particular embodiments, the seal member 300 includes a plurality of such windows 340. As described herein in more detail, such compression or axial movement occurs when an axial force is applied to the proximal end 310 of the seal member 300 such as for example a portion of the coupling device being removably coupled to the coupling end 110 of the proximal housing 100.

Each window 340 in the seal member 300 is arranged so it extends between an exterior surface 304 of the seal member 300 and the inner seal member cavity 302 thereof whereby fluid can flow in one direction through each of the windows into the inner cavity (such as when fluid is being injected into the patient) or can flow in the opposite or another direction through the inner cavity and out through the one or more windows 340 (such as when fluid is being extracted from the patient such as for sampling purposes). The number, shape and size of windows 340 is set so that the resultant cross-sectional area is appropriate to establish the desired fluid flow conditions (e.g., desired pressure loss and flow volume).

The proximal end 310 of the seal member 300 includes one or more raised sections 312 (FIGS. 2B and 2C) arranged about a centrally positioned chamber 313 and one or more passages or channels 314 between each of the one or more raised sections and which are fluidly coupled with the central chamber. The proximal end 310 also includes a septum 316.

The raised sections 312 and the channels cooperate so that when the sealing portion 330 of the seal member 300 is displaced from the proximal housing seating surface 114 (FIG. 2H), one or more flow paths (FIG. 15C) are established between the centrally positioned chamber 313. Thus, when the sealing portion 330 is displaced from the seating surface 114 of the proximal housing 100 corresponding to a valve open condition, fluid can flow from/to the coupling end 110 of the proximal housing, through the centrally positioned chamber 313 and the channels 314; about the seal member 330 and through the seal member windows 340, through the seal member inner cavity 302, through a portion of the distal housing inner cavity 230 (e.g., see FIG. 2I) and to/from the open end 252 of the tubular member 250.

Figure 2I:
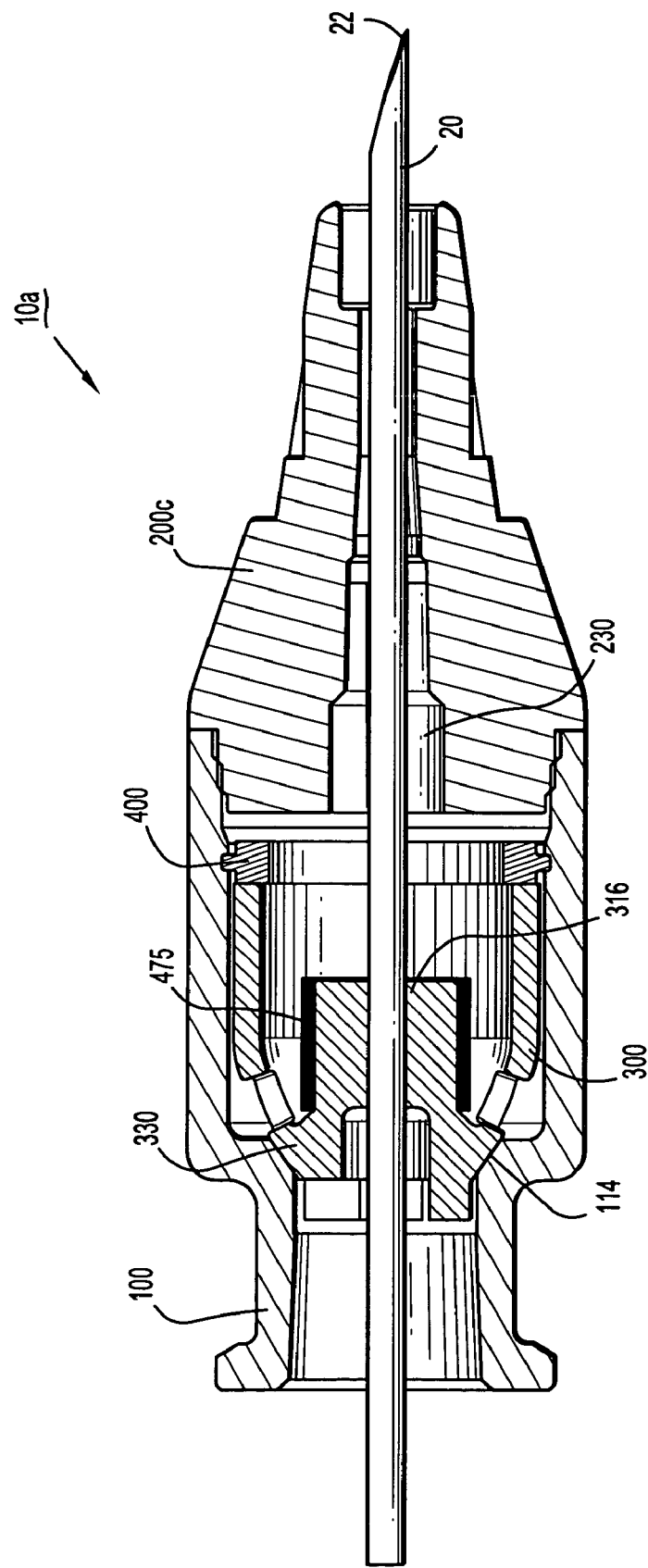
FIG. 2I is an assembled, cross-sectional, plan view of the aspect of the IV catheter of FIG. 2A with the stylet in place and the tubular member omitted for simplicity.
Figure 15A:
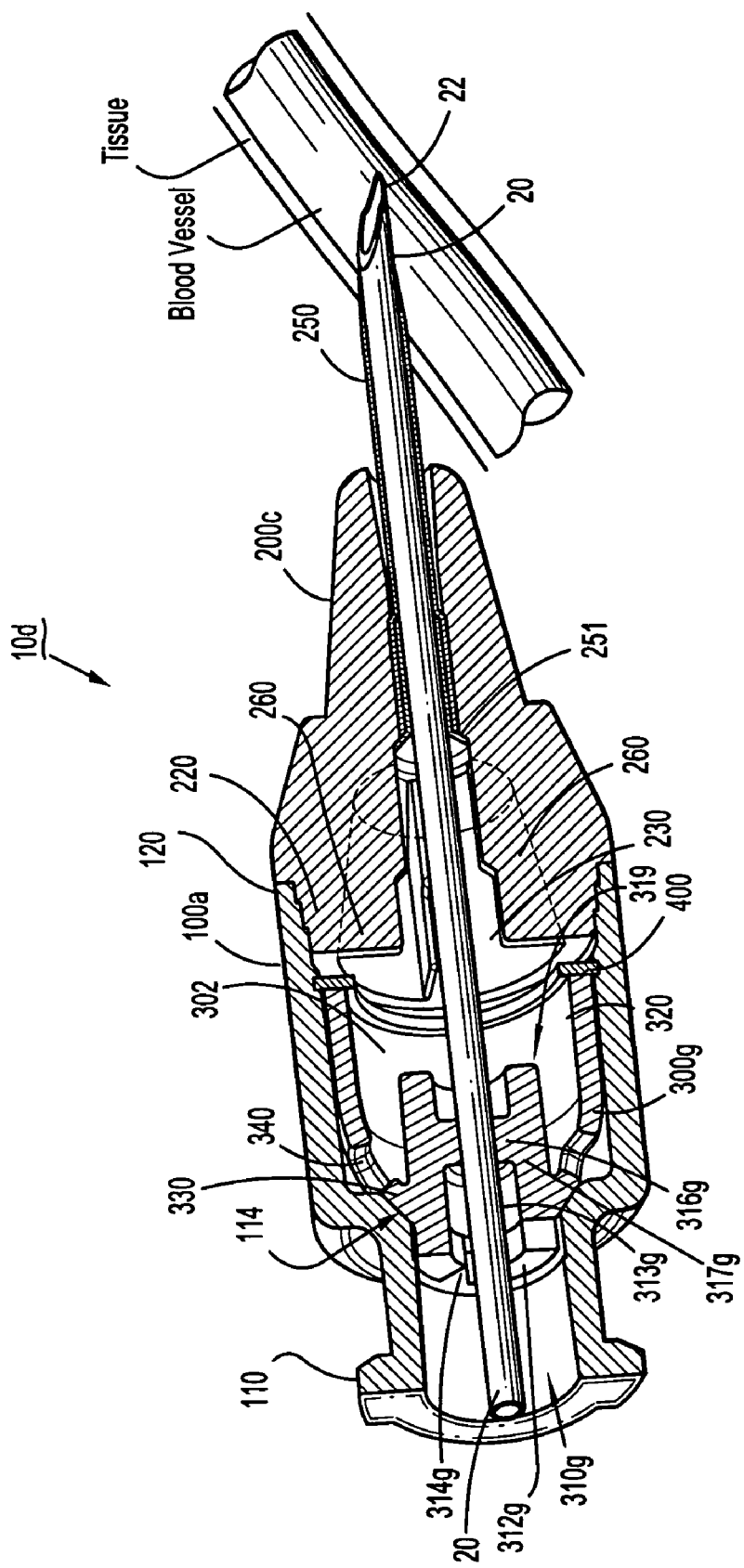
FIGS. 15A, B are cross-sectional views of the in-line valve IV catheter illustrating an exemplary use of such an IV catheter.

Prior to use as an IV catheter, and as illustrated in FIG. 2I and 15A, a stylet/sharp/cannula 20 is disposed to pass through the centrally positioned chamber 313, through the septum 316 and through the seal member inner cavity 302. As also shown in FIG. 2A, the stylet/sharp/cannula 20 also passes through the second portion 132b of the proximal housing 100, the centrally located opening or through aperture in the locking ring member 400, through the inner cavity 230 of the distal housing 200 and out through the tubular member 250. The septum 316 and the proximal end 310 of seal 300 are made of a resilient material(s) that will re-seal themselves after the stylet/sharp/cannula 20 is withdrawn through the septum. It is contemplated that the sharp end of the stylet/sharp/cannula 20 can be used to form the opening in the septum through which it would pass or another device or instrumentality can be used to form the opening initially in the septum 316 and thereafter the stylet/sharp/cannula 20 would be inserted through this initially formed opening by the opposite end or the sharp end of the cannula.

As shown in more clearly in FIG. 2I, the proximal end 310 of the seal member 300 extends into the second portion 132b of the inner cavity 130 of the proximal housing 100 when the sealing portion 330 of the seal member 300 is in sealing engagement with the seating surface 114 which corresponds to the valve closed condition. In use, when a portion of a syringe or other device 2 (FIG. 15B,C) is inserted into the opening in the coupling end 110 of the proximal housing 100, the syringe or other device portion contacts and pushes against the proximal end 310 of the seal member 300, more specifically contacts and pushes against the raised sections 312 of the proximal end. Such contacting or pushing thereby causes a force (e.g., an axial force) to be applied to the seal member proximal end 310 to thereby axially displace or move the sealing portion from the seating surface 114 as illustrated for example in FIGS. 15C. As also indicated herein, such syringe or other device would be secured (i.e., removably secured) to the coupling end 110 of the proximal housing 100 using any of a number of techniques known to those skilled in the art (e.g., a luer connection).

As indicated above, such displacing opens up the valve embodied in the in-line valve IV catheter assembly 10 and also creates a flow path through the in-line valve IV catheter assembly. When the valve is thus opened, a fluid pathway is thereby established between the syringe or other device and the open end 252 of the tubular member 250. In this way, fluid can flow in either direction through the in-line valve IV catheter assembly as described in more detail herein so that fluid can be introduced into the blood vessel in which the tubular member 250 is inserted into or so a fluid sample can be extracted from such a blood vessel.

When the syringe or other device is decoupled from the coupling end 110 and removed from the second portion 132b (FIG. 2A), the force that was acting on the proximal end 310 of the seal member 300 is removed. When such force is removed, the resiliency of the seal member 300 causes the seal member to move axially towards the seating surface 114 (i.e., away from the locking ring member 400) until the sealing portion 330 thereof sealingly engages the seating surface 114 (FIG. 2H) of the proximal housing 100. In this way, the valve formed by the cooperation of the proximal housing 100, the seal member 300 and the locking ring member 400 is again closed preventing flow of fluid through the in-line valve IV catheter assembly 10a. The foregoing described operation of coupling a syringe or other device to the proximal housing 100 can be repeated as and when needed/desired by medical personnel.

Referring now to FIGS. 2A-I, there are several views of another aspect of an in-line valve IV catheter 10a and various parts such as a seal member 300 with a septum 316 and a compression member 475. The compression member 475 is disposed about the septum 316 so that a radially compressive force is applied to the septum 316. A beneficial effect of enhancing the ability of the septum 316 to reseal is to minimize the potential for leakage through the septum 316 after removal of the stylet/sharp/cannula 20. Such an in-line valve IV catheter 10a also is shown with an insertion stylet/sharp/cannula 20 that is inserted therethrough (e.g., see FIG. 2I).

In a preferred embodiment, the septum 316 has a preformed slit or passage 301 for the stylet/sharp/cannula 20 and the compression member 475 has an inner diameter 477 (FIG. 2G) smaller than the outer diameter 323 (e.g., see FIG. 2E) of the septum 316 to provide adequate restorative force. A plurality of factors govern the ideal sizing relationship between the inner diameter 477 of the compression member 475 and outer diameter 323 of the septum 316 such as the material of the septum 316, the manufacturing tolerances of the septum 316 and compression member 475, the diameter of the stylet/sharp/cannula 20, the ease of assembly and like factors as would be appreciated by those of ordinary skill in the pertinent art. Before insertion of the stylet/sharp/cannula 20, the ratio of inner diameter 477 of the compression member 475 to the outer diameter 323 of the septum 316 could be approximately 1.0 and insertion of the stylet/sharp/cannula 20 would create compression. In one embodiment, the ratio (cannula not in place) is in the range of approximately 0.79 to 0.92, and most preferably between 0.82 to 0.88.

In a further embodiment, the axial width of the collar 475 is longer than the axial width of the septum 316 such that the entire septum 316 is uniformly compressed, as the septum expands axially due to the radial compression. Preferably, the compression member 475 is composed of a rigid bio-compatible material such as stainless steel, plastic (e.g. polycarbonate) or like material to lend circumferential rigidity and strength to the septum.

During assembly, the septum 316 is fit within the compression member 475 and the stylet/sharp/cannula 20 passes through the septum 316 in a ready-to-insert position. In further embodiments, the compression member 475 is formed of an elastic or semi-resilient material having different elastomeric characteristics (e.g., thickness, resiliency) than the seal member so that the septum is similarly maintained in a radial compression.

Without being bound to any particular theory or principle of science, the compression member 475 enhances the ability of the septum 316 to self-close or self-seal itself after the insertion stylet/sharp/cannula 20 is removed from the septum 316. Also, the compression member 475 enhances the ability of the septum 316 to limit or resist propagation of any tears that may originate in the septum 316. These advantageous effects are attributed to the presence of the compression member 475 and the effect such a structure has on enhancing or increasing the radial stiffness of the septum 316.

In the event that the storage extends for a number of years, the radial compression provided by the compression member 475 in tandem with the resiliency and sealing properties of the septum 316 establishes an effective sealing force after removal of the stylet/sharp/cannula 20 so as to thereby cause the opening 301 in the septum 316 for the stylet/sharp/cannula 20 to reseal itself. It is also envisioned that the compression member 475 can be effectively used with this embodiment and other similar embodiments shown herein and elsewhere. Additionally, technology is also disclosed herewith to prevent the potential for blood leakage following removal of the insertion stylet/sharp/cannula 20. Such technology may be used solely or in conjunction with the other devices and structures herein.

Figure 3A:
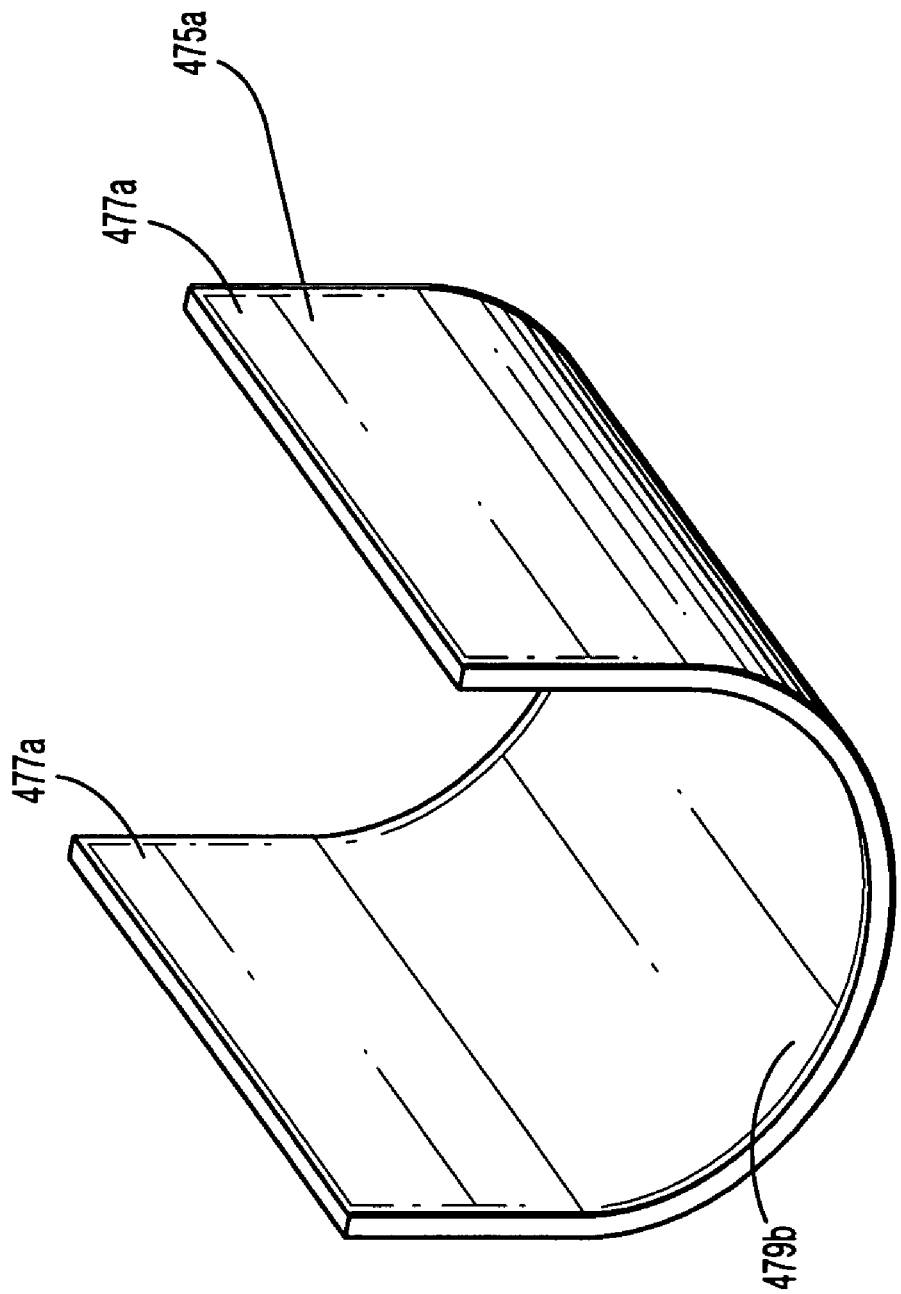
FIG. 3A is a perspective view of another compression member for use in the IV catheter.
Figure 3B:
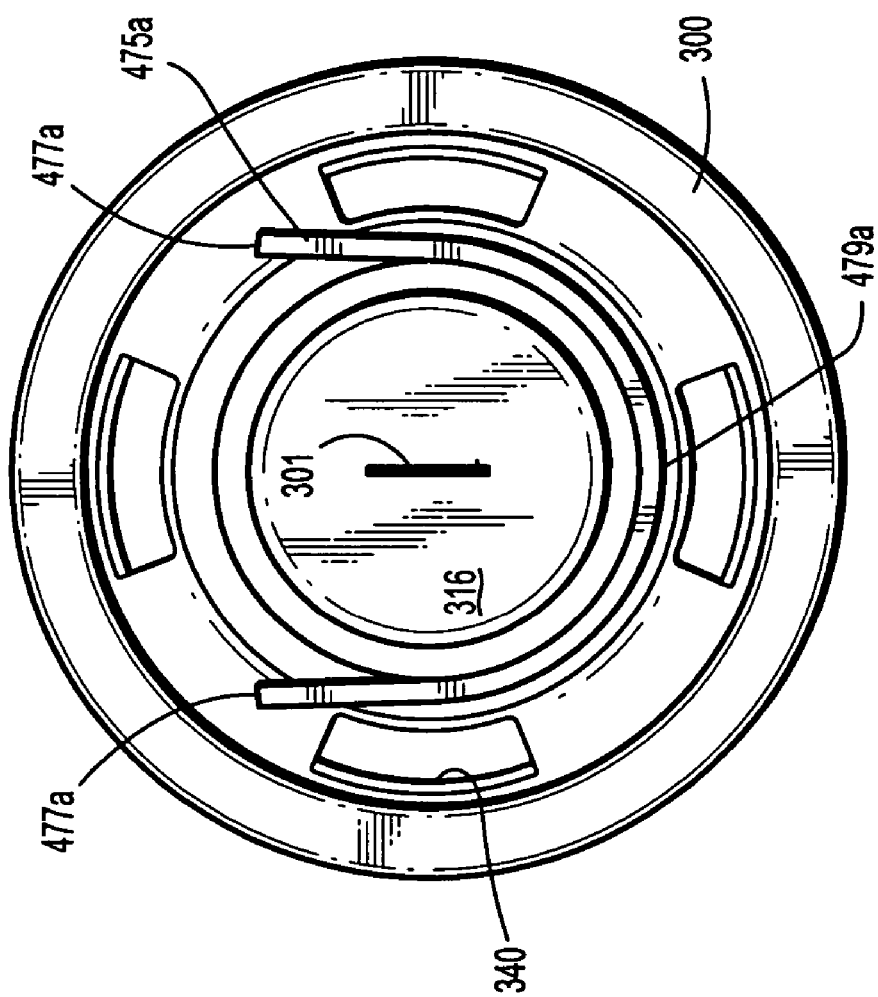
FIG. 3B is an assembled, distal cross-sectional end view of an IV catheter with the compression member of FIG. 3A in place on a septum.
Figure 4:
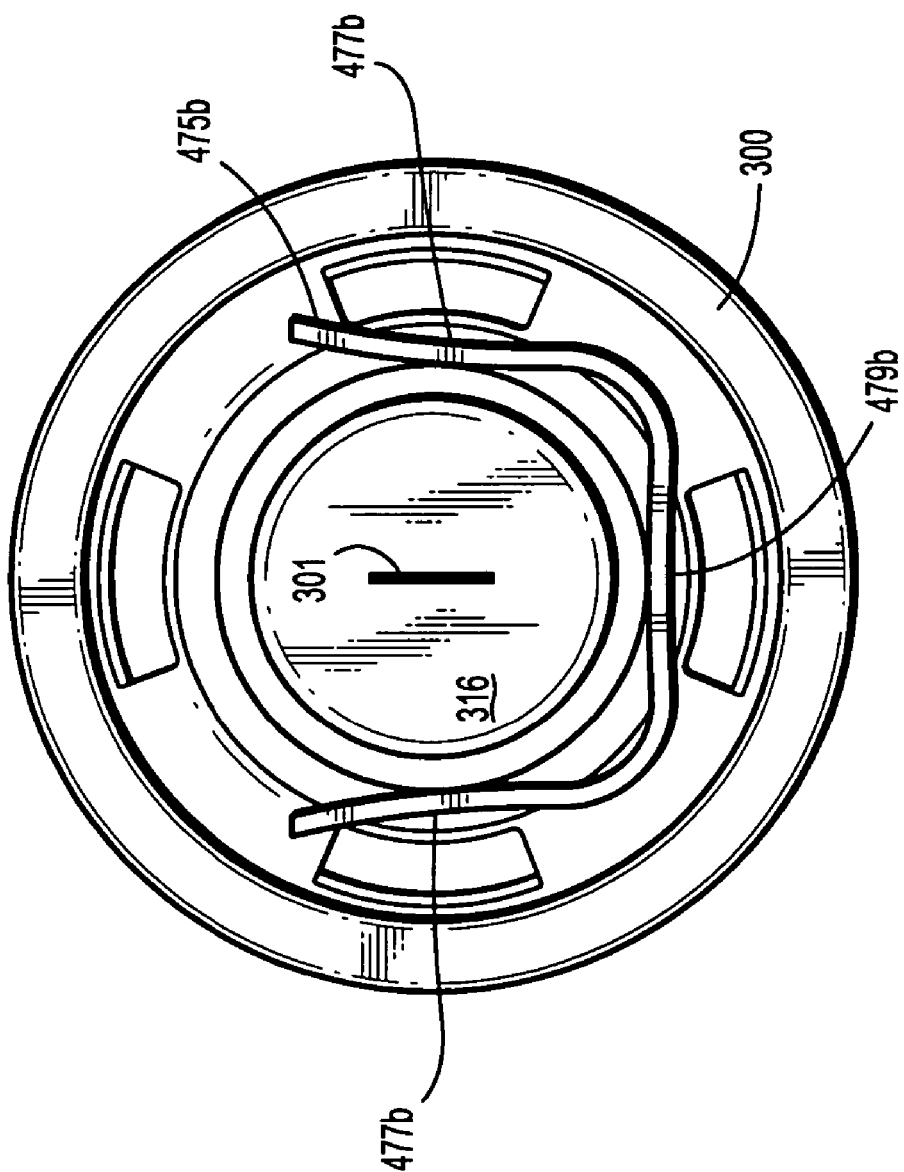
FIG. 4 is an assembled, distal cross-sectional end view of an IV catheter with still another compression member in place on a septum.

Referring to FIGS. 3A and 3B, another embodiment of a compression member 475a is shown in perspective and disposed on a septum 316, respectively. The compression device 475a is roughly U-shaped with two relatively straight legs 477a depending from an arcuate intermediate portion 479a. Preferably, the legs 477a are parallel the elongated slit 301 to provide compression substantially only perpendicular thereto. The U-shaped compression member 475a provides easier assembly and is more efficient to fabricate in certain circumstances. As one possible exemplary variation of the U-shaped member 475a, FIG. 4 shows another U-shaped member 475b having a relatively straight intermediate portion 479b, which provides even less, if any, pressure along the axis of the elongated slit 301.

Figure 5:
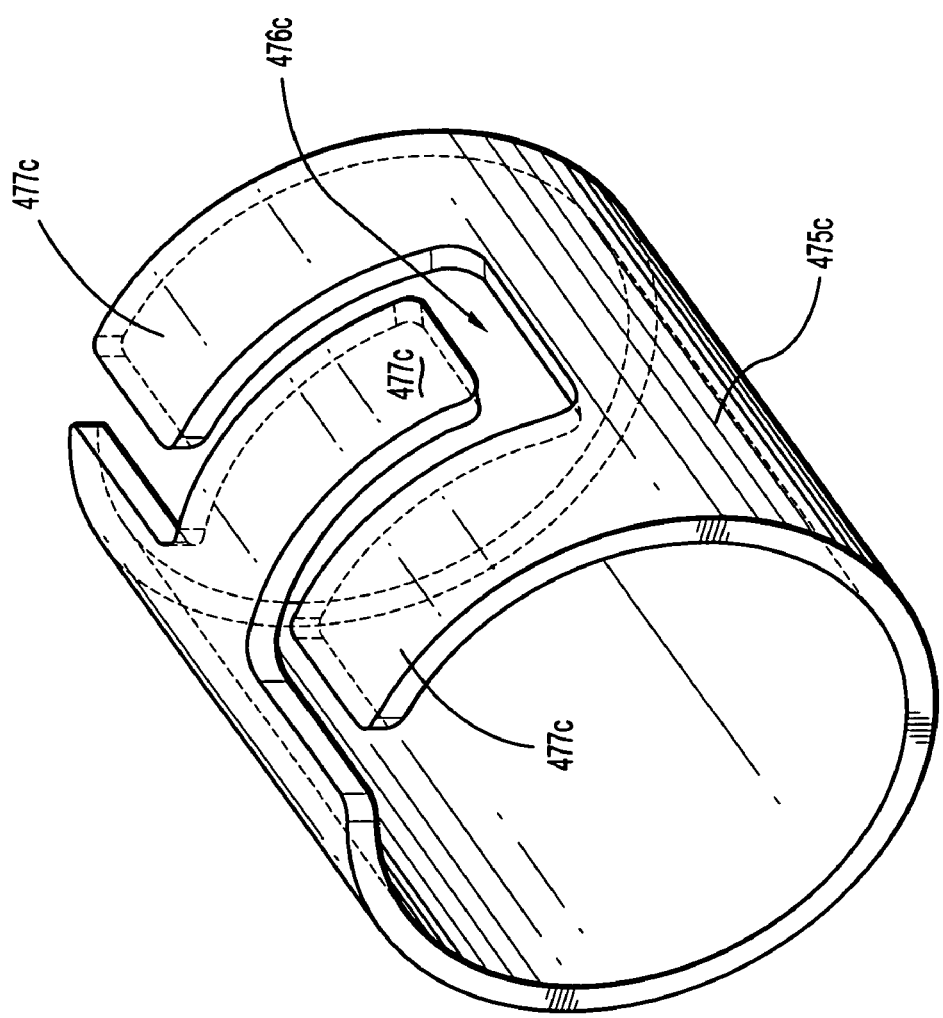
FIG. 5 is a perspective view of another compression member for use in an IV catheter.
Figure 6:
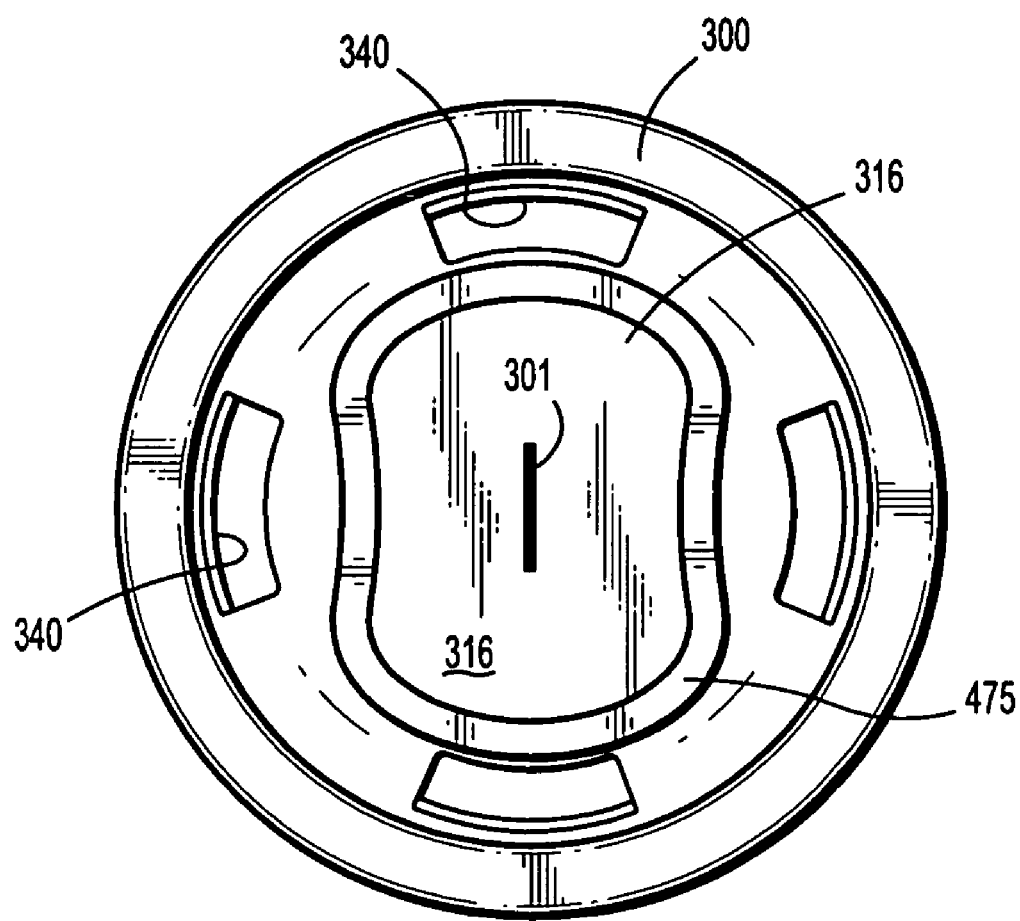
FIG. 6 is an assembled, distal cross-sectional end view of an IV catheter with another compression member in place on a septum.

Referring to FIG. 5, another embodiment of a compression member 475c is shown in perspective view. The compression member 475c is collar-shaped and defines a channel 476c that acts as an expansion joint for radial expansion and/or contraction. Preferably, the channel 476c is non-linear so that interlocking legs 477c are formed. As a result of the ability to radially expand and contract, the compression member 475c is easily positioned. Upon proper placement, the compression member 475c may be crimped or squeezed for securement on the septum 316. For example, FIG. 6 shows a distal end view of a compression member 475 (e.g., 475a or 475c) that has been crimped onto a septum 316.

Figure 7:
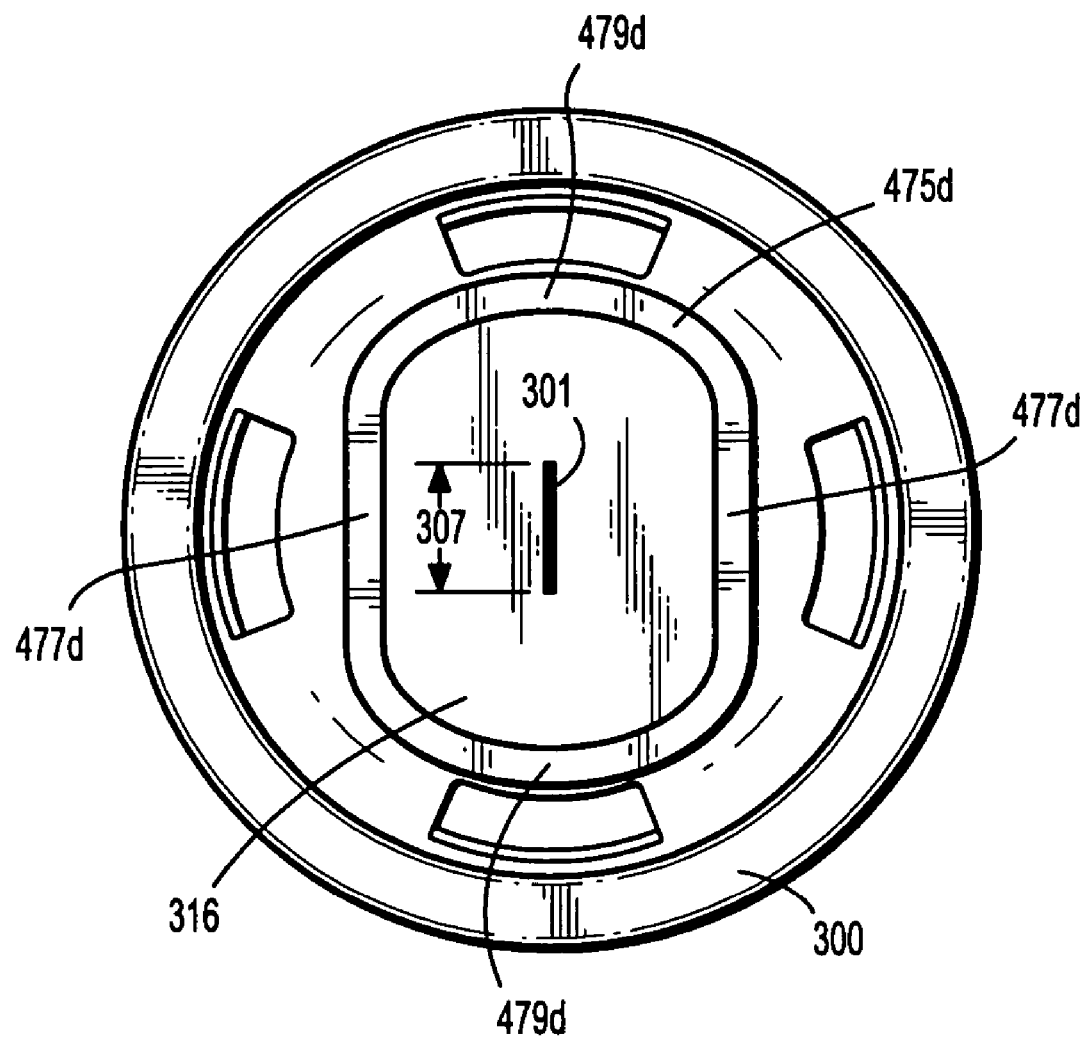
FIG. 7 is an assembled, distal cross-sectional end view of an IV catheter with still another compression member in place on a septum.
Figure 8:
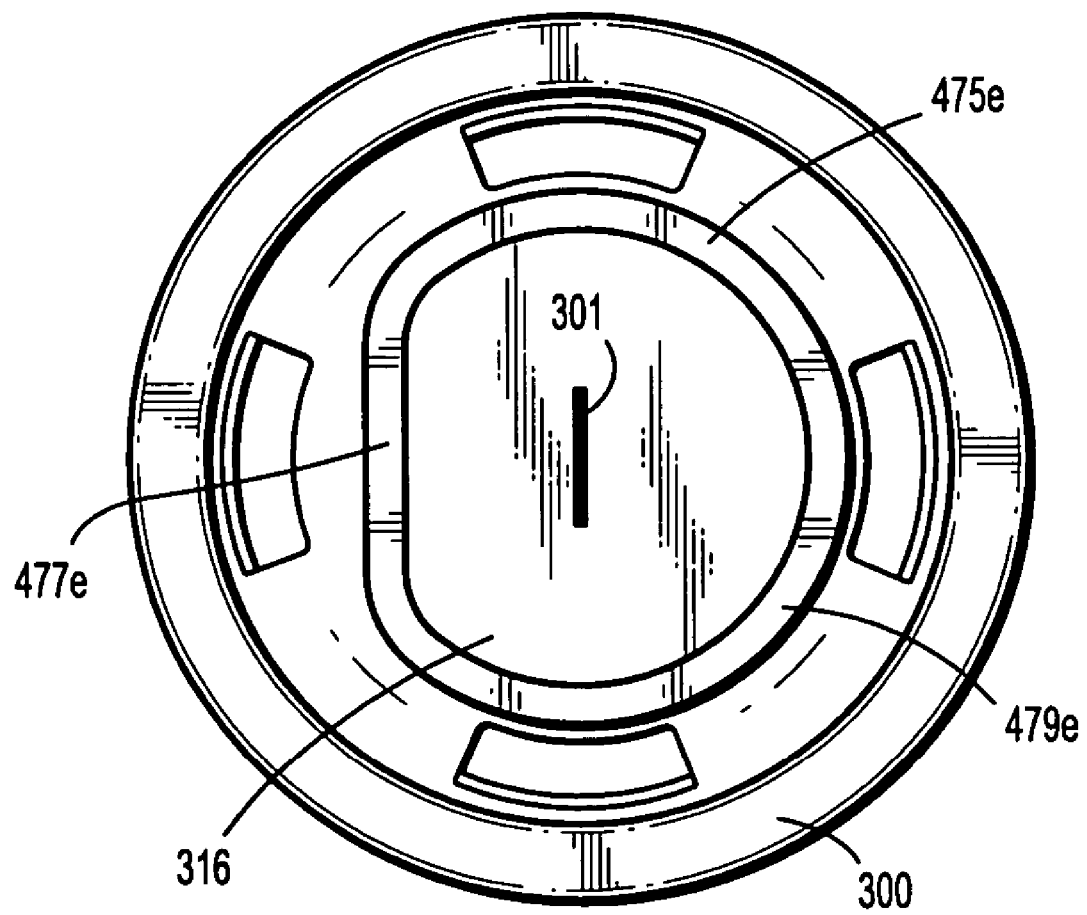
FIG. 8 is an assembled, distal cross-sectional end view of an IV catheter with still another compression member in place on a septum.

Referring to FIG. 7, another embodiment of a compression member 475d is shown disposed on the septum 316. The compression member 475d has two opposing flat sides 477d interconnected by semi-circular sections 479d such that the opposing flat sides 477d apply substantially uniform compression along the height 307 of the elongated slit 301. In other words, the septum 316 defines an elongated slit 301 having a height 307 substantially parallel to the two opposing flat sides 477d. Referring to FIG. 8, still another embodiment of a compression member 475e is shown disposed on a septum 316. The compression member 475e has a single flat portion 477e with the remainder 479e being generally arcuate. Generally, the compression members of FIGS. 6-8 are formed as collars, rings or sleeves. However, it is also envisioned that such members could be sections of wire, which may be crimped or squeezed into position on the septum.

Figure 9C:
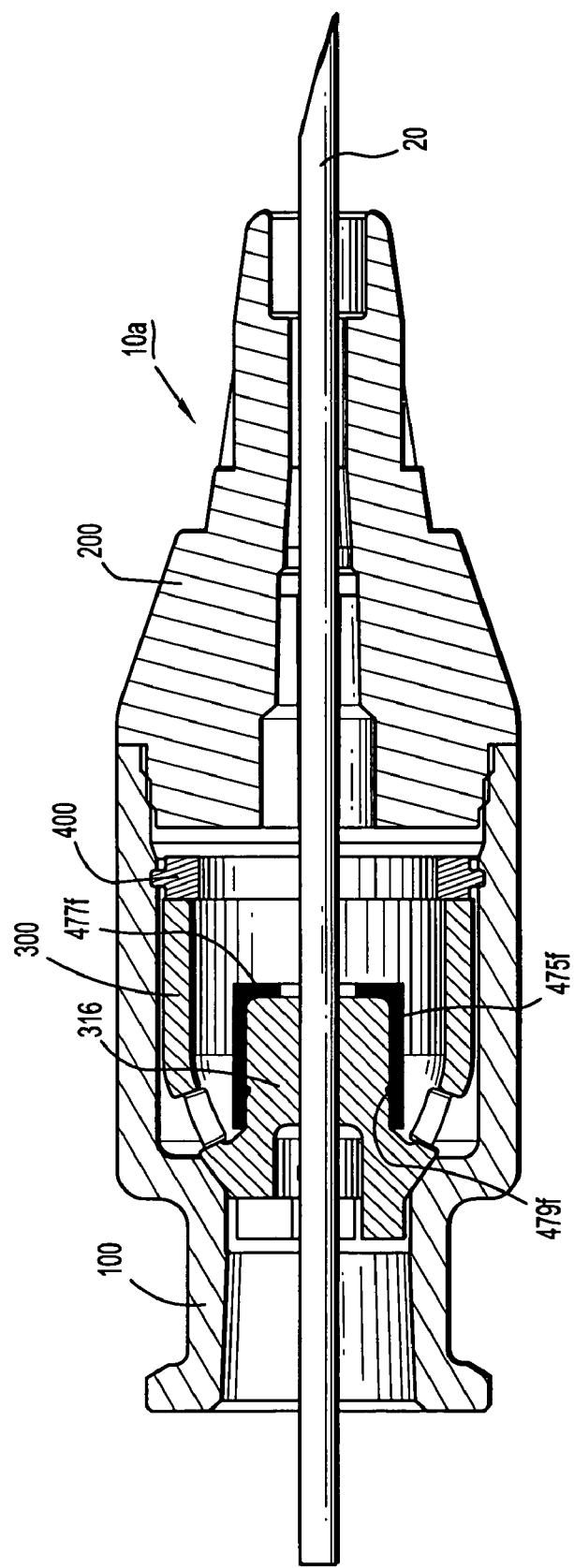
FIG. 9C is an assembled, cross-sectional, plan view of the aspect of the IV catheter of FIG. 9B with the stylet in place.

Referring now to FIG. 9A, another version of a compression member 475f is shown in a perspective view. FIGS. 9B and 9C show assembled side cross-sectional views of an IV catheter 10a with the compression member 475f before and after insertion of the stylet 20, respectively. This compression member 475f has a very similar tubular structure with that as described above but further includes a flange 477f on the distal end and one or more friction elements 479f on the inner diameter of the proximal end. When the collar 475f is disposed on the septum 316, the septum 316 is substantially within the region intermediate the flange 477f and friction elements 479f.

The flange 477f serves to facilitate proper positioning of the collar 475f by acting as an effective stop during assembly. In other words, the collar 475f is mounted onto the septum 316 until the proximal inner surface of the flange 477 is flush with the distal end of the septum 316. Since the spacing between the flange 477f and friction elements 479f and size of the septum 316 are known, such assembly assures that the septum 316 is substantially between the flange 477f and friction elements 479f. In another embodiment, the mechanism to act as a stop during assembly is one or more projections on the collar. Such projections could be as simple as a single finger-like projection, barbs or arcuate shaped projections as long as ample friction is created to prevent over-insertion of the collar.

Once properly positioned, the friction elements 479f serve to provide a retentive force on the collar 475f by creating increased friction with the seal member 300. Preferably, the friction elements 479f are intermittently spaced along the inner diameter of the collar 475f and may be located at the same axial location or be axially spaced with respect to each other. The friction elements 479f are sized and positioned to provide sufficient retentive force such that even a single friction element could be effective. In one embodiment, the friction elements 479f only retain the collar 475f as the collar 475f is configured to seal the septum 316 without the friction elements 479f surrounding the septum 316.

It is currently preferred to have both the outer surface of the septum 316 and the inner surface of collar 475f smooth, to maximize contact area between the two components. In an alternative embodiment, the friction elements are one or more raised diamond-shaped portions. In another embodiment, the friction elements comprise a roughened surface on the inner diameter of the collar so that a nominal inner diameter is present but the surface lacks smoothness and uniformity. A roughened surface on the inner diameter of the collar appears to be desirable when the septum outer surface is roughened, especially if the roughened surfaces are complementary and/or interlocking. For another example, in FIG. 10, a compression member 475g has an annular inner ring 479g to provide the retentive force with the septum 316. Various other shapes, such as a substantially circular asymmetrical ring with a plurality of substantially flattened portions, would function appropriately as would be appreciated by those of ordinary skill in the art upon review of the subject disclosure. In another embodiment, the constrictor is at least one rigid arcuate section retained against the seal member about the septum by an elastic band. In still another embodiment, compression is applied to the septum by a split ring having end portions that overlap and protrude such that upon movement of the end portion together, a diameter of the split ring increases to ease assembly. In another embodiment, compression is applied by a staple formed tightly around the septum. The staple may be various shapes adapted to compress the septum in a desirable manner such as U-shaped and the like.

Figure 11:
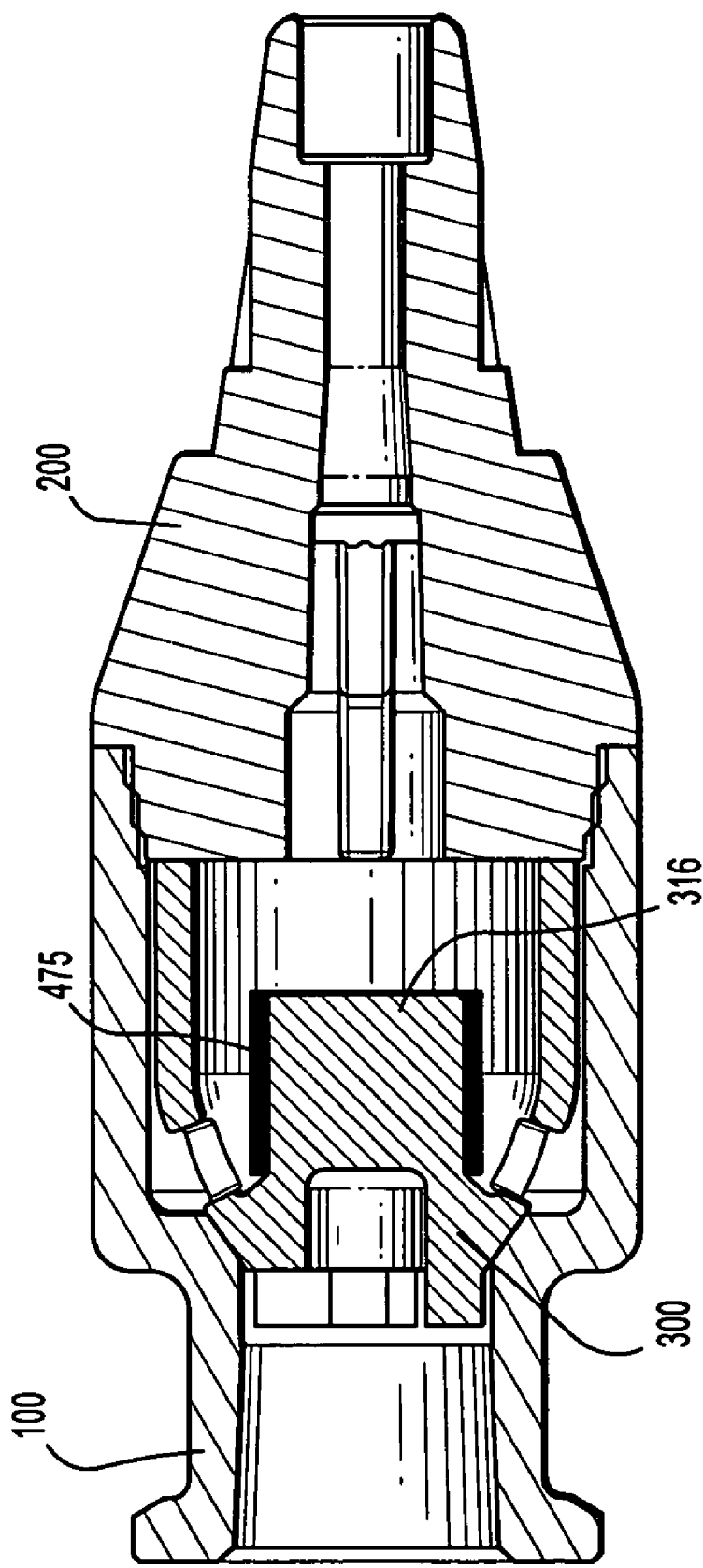
FIG. 11 is an assembled, cross-sectional view of an IV catheter having a two-piece housing with the compression member in place.

It is also envisioned that various compression members may be deployed with different septums and housings. For example, in FIG. 11 the IV catheter does not have a locking ring member 400, i.e., the IV catheter is a two-piece housing design including the proximal housing 100 and the distal housing 200 that are secured to each other so as to form an integral unit and so as to form a pressure boundary.

Figure 12A:
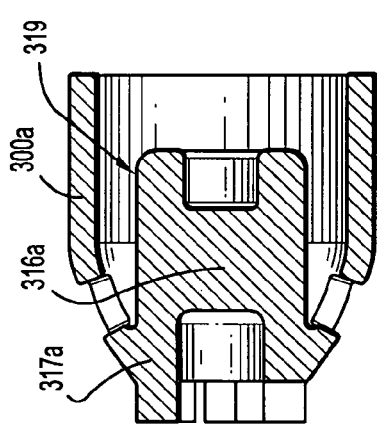
FIG. 12A is a cross-sectional view of another seal member with a remote septum for use in an IV catheter.
Figure 12B:
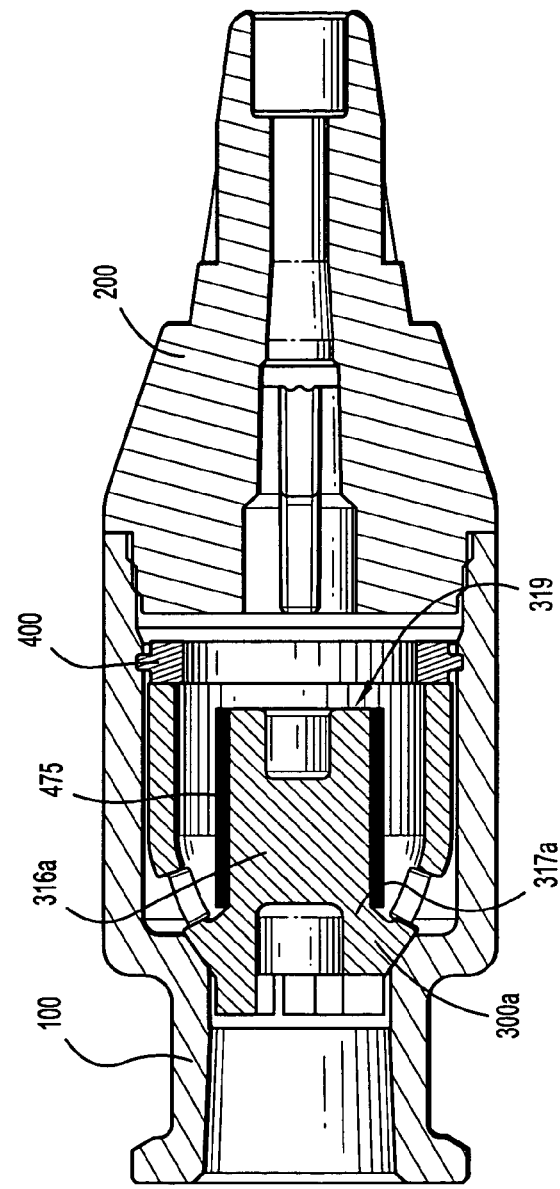
FIG. 12B is an assembled, cross-sectional, plan view of an IV catheter with the compression member of FIG. 2F in place.
Figure 12C:
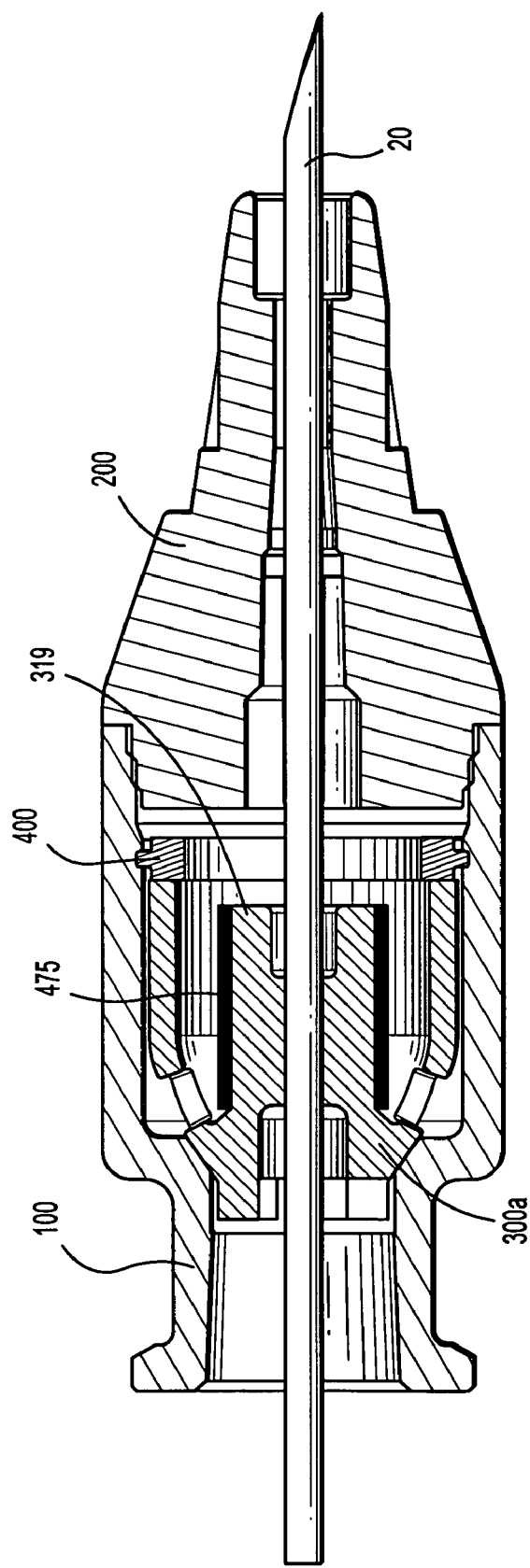
FIG. 12C is an assembled, cross-sectional, plan view of the aspect of the IV catheter of FIG. 12B with the stylet in place.

In FIG. 12A, another seal member 300a for use with a septum collar 475 is shown in cross-sectional view. Side wall(s) 317a extends beyond the septum 316a so as to create a collar portion 319 that extends outwardly from and beyond the septum 316a. Without being bound to any particular theory or principle of science, the collar portion 319 enhances the ability of the septum 316a to self-close or self-seal itself after the insertion stylet/sharp/cannula 20 is removed from the septum 316a. In FIGS. 12B and 12C the seal member 300a is shown assembled in an IV catheter with and without the stylet 20, respectively.

Figure 13A:
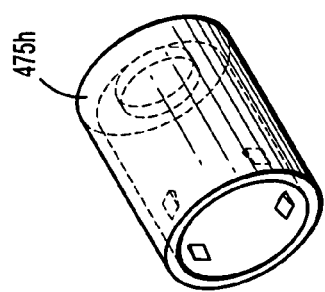
FIG. 13A is a perspective view of yet another compression member for use in an IV catheter.
Figure 13B:
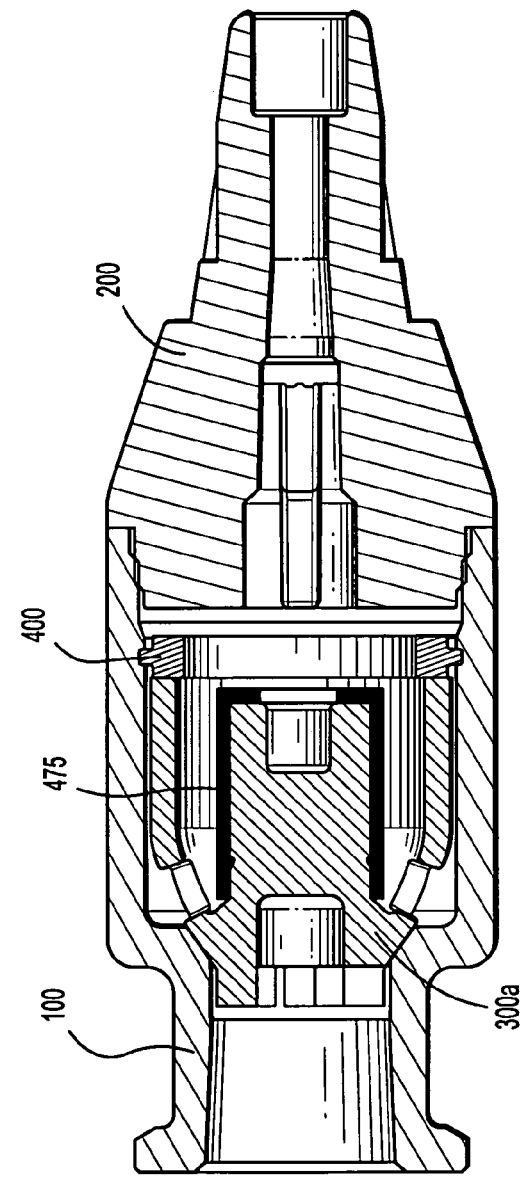
FIG. 13B is an assembled, cross-sectional, plan view of an IV catheter with the compression member of FIG. 13A in place.
Figure 13C:
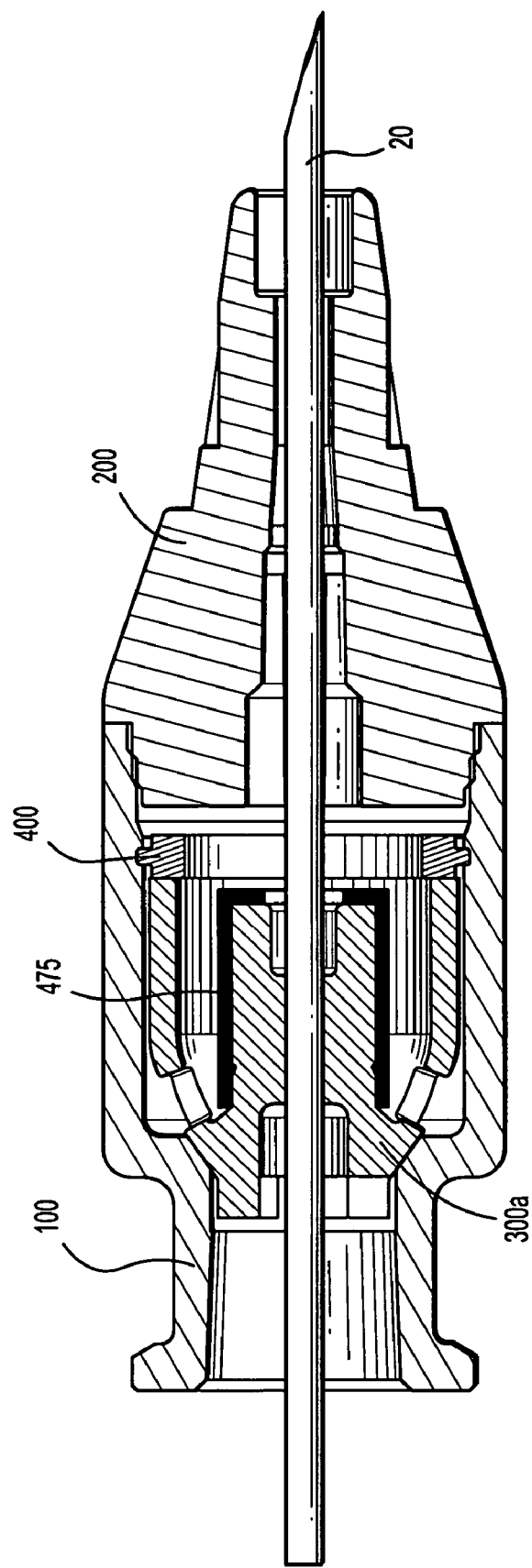
FIG. 13C is an assembled, cross-sectional, plan view of the aspect of the IV catheter of FIG. 13B with the stylet in place.

In FIG. 13A, another version of a compression member 475h is shown in a perspective view for use with a seal member 300a such as shown in FIG. 12A. FIGS. 13B and 13C show assembled side cross-sectional views of an IV catheter 10h with this compression member 475h before and after insertion of the stylet 20, respectively. This compression member 475h has a very similar structure with that as described above with respect to compression member 475f.

Figure 14:
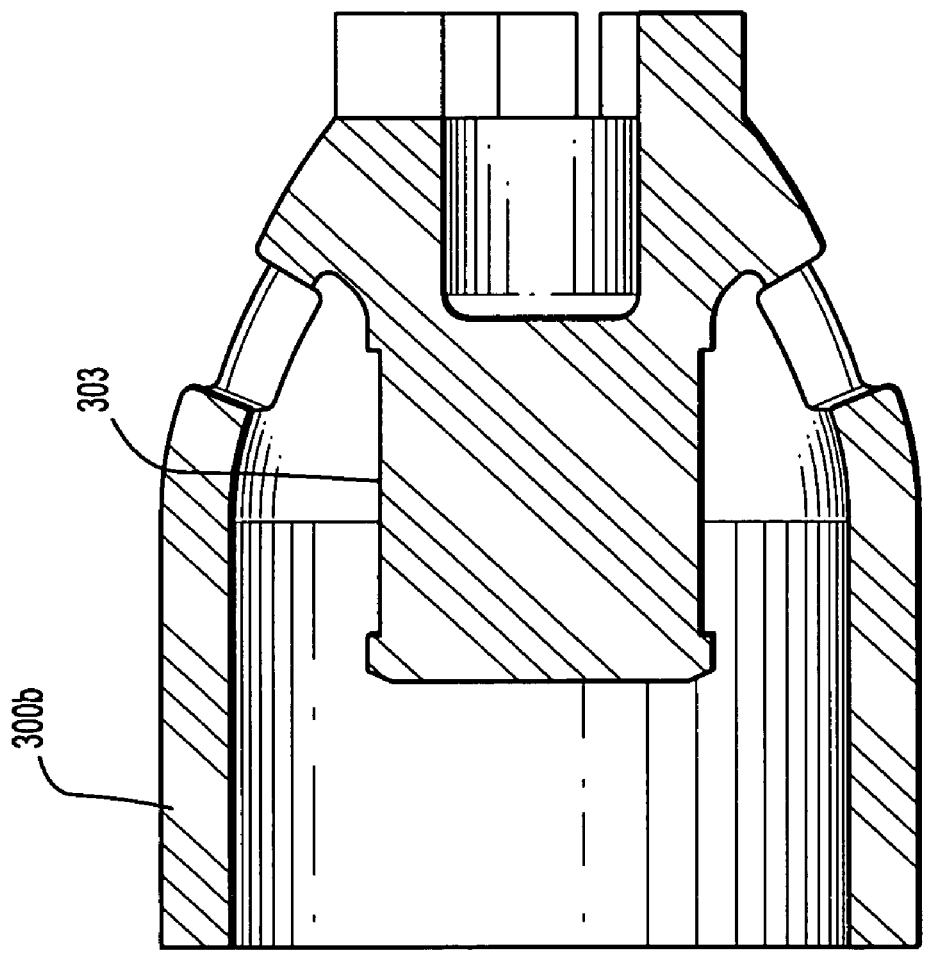
FIG. 14 is a cross-sectional view of yet another seal member with a remote septum for use in an IV catheter.

Still another embodiment of a seal member 300b is shown in cross-sectional view in FIG. 14. The primary difference of this seal member 300b is an annular groove 303 for receiving a compression member (not shown). In another embodiment, the seal member is configured so as to include an outer annular ridge that is disposed about the septum to enlarge a radius thereof approximate the point of compression by the compression member. In another embodiment, the septum extends axially along the stylet in one or more directions. The septum may also form a pre-set axial passageway. The passageway may be symmetrical or asymmetrical such as, without limitation, a tapered slit with a relatively smaller proximal end. It is also envisioned, without limitation, that the compression member may be a plurality or combination of items such as a crimped ring, at least one rigid arcuate section retained against the septum by an elastic band, a split ring having end portions that overlap and protrude such that upon movement of the end portion together, a diameter of the split ring increases, and/or a U-shaped staple prior to placement, wherein upon placement each end of the staple is formed tightly around the septum.

It should be noted that it is contemplated, and thus within the scope of the present invention, for the subject invention to further comprise device kits that include one or more of the in-line valve IV catheters and which device kits maintain the in-line valve IV catheter in sterile conditions during shipment from the manufacturing facility and in storage prior to use. Such device kits also can further include other instrumentalities, devices or materials normally associated with use of the catheter, including but not limited to tubing, cleaning materials to establish aseptic conditions prior to insertion of the IV catheter and/or clips/clamps or the like for regulating flow of fluid from an IV drip to the patient.

Figure 15B:
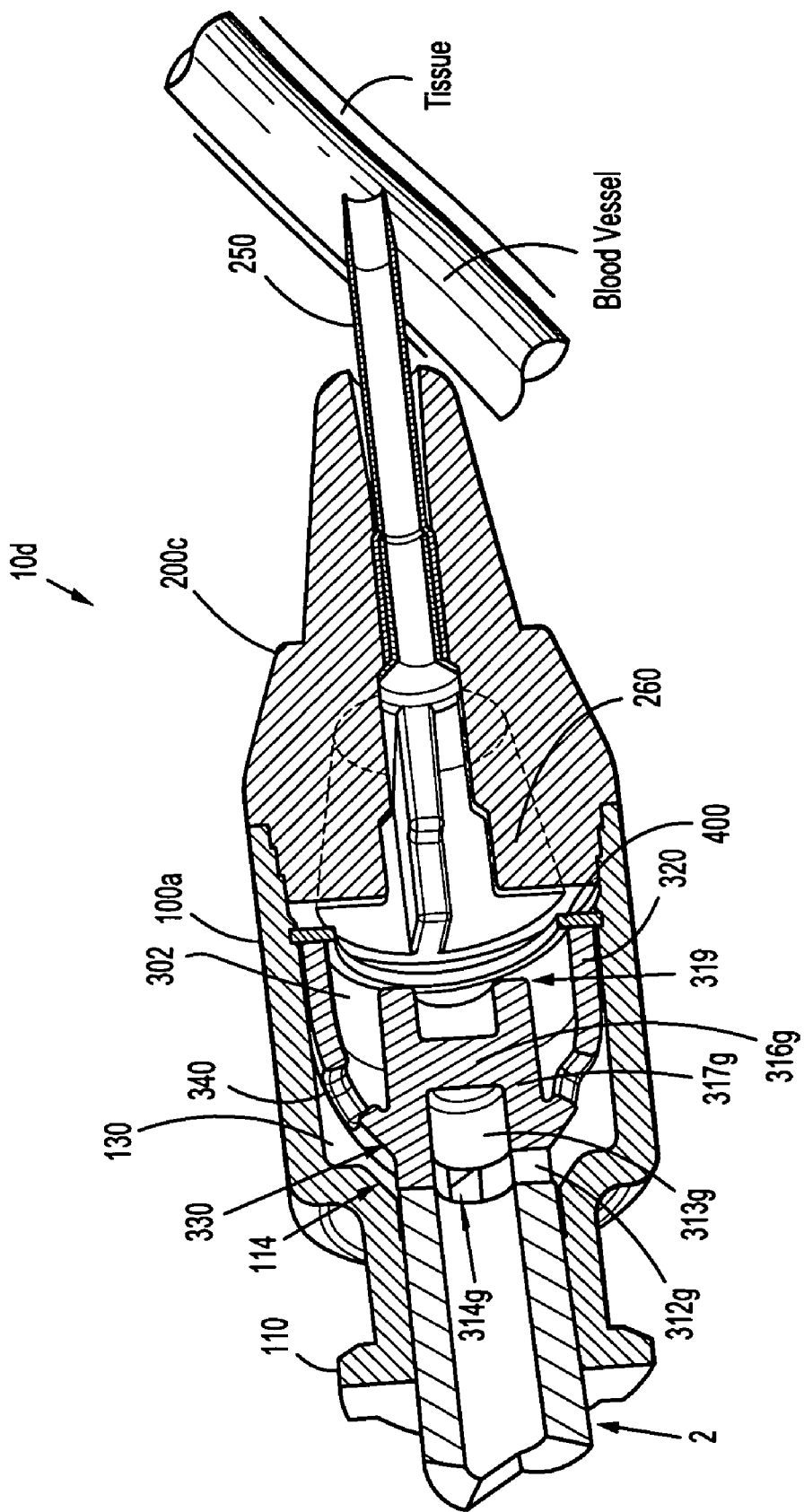
FIG. 15C is an annotated cross-sectional view of the in-line valve IV catheter of FIG. 11B illustrating fluid flow in one direction when the sealing portion of the seal member is displaced responsive to the insertion of a nose of a luer device.
Figure 15C:
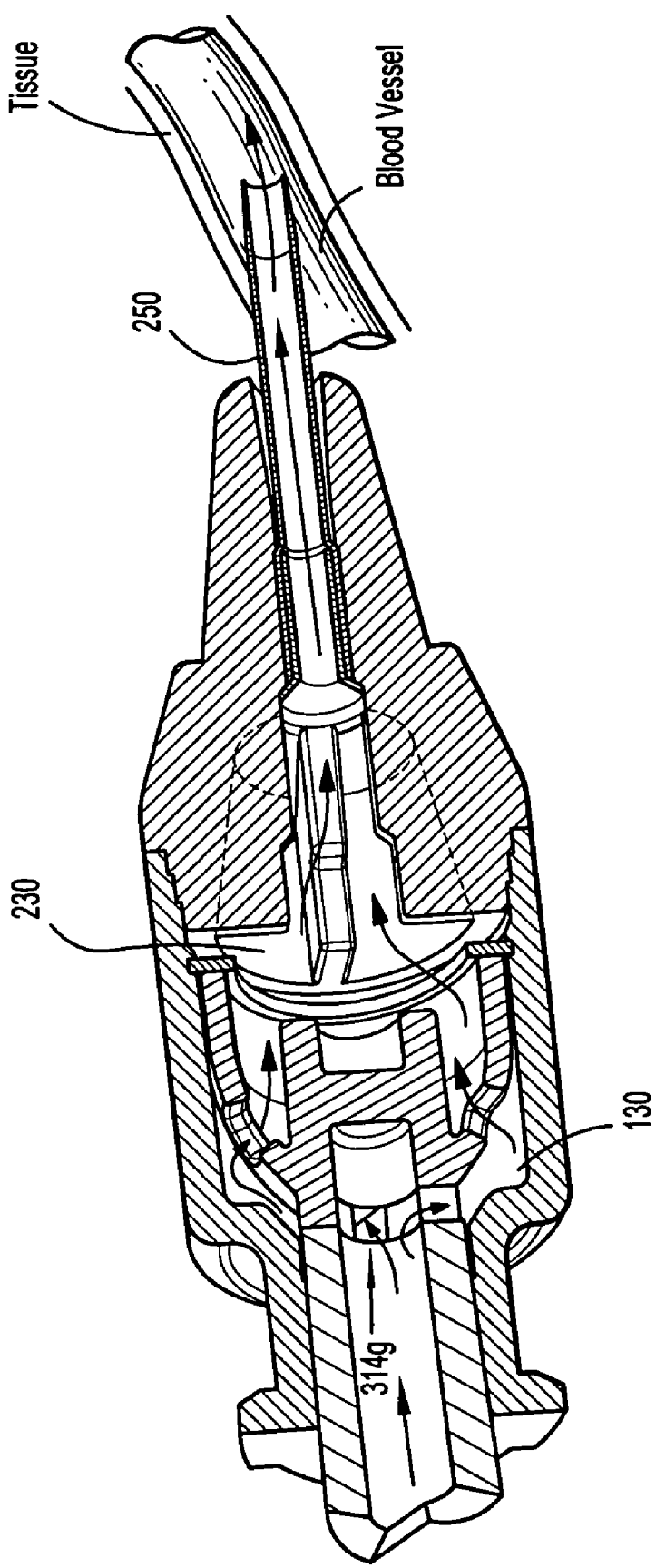

Referring to FIGS. 15A-C, cross-sectional views of the in-line valve IV catheter illustrating an exemplary use and fluid flow of such an IV catheter are illustrated. Reference shall be made to U.S. Provisional Patent Application No. 60/726,026, filed Oct. 11, 2005, and the foregoing discussion regarding details or characteristics regarding the IV catheter not otherwise described or detailed herein. Additionally, although not shown, a compression member, as discussed above, could be advantageously used about the septum 316g.

Initially, the medical personnel would prepare the in-line valve IV catheter 10d for use in accordance with the procedure to be performed including removing the catheter from any device kit. The medical personnel would then perform the usual and customary actions to identify a potential target insertion site (e.g., locating a vein in which the open end of the tubular member 250 would be located) and to prepare the exposed skin of the patient surrounding the injection site for insertion of the needle into the patient's skin. Such preparing can include, for example, performing a cleaning and/or sterilizing operation (e.g., swabbing the skin with alcohol swab, applying a sterilizing solution).

Thereafter, the medical personnel would locate the sharp end 22 or point of the introducer needle 20 on the patient's body at the target insertion site. Following such localizing, the medical personnel would insert the sharp end 22 or point of the introducer needle 20 into and through the skin of the patient and the wall of the blood vessel such that the needle sharp end resides within the targeted blood vessel of the patient as shown in FIG. 15A.

As indicated herein, once the sharp end 22 of the introducer needle 20 is in the blood vessel, the pressure of the blood within the patient causes blood to flow back or flashback in a proximal direction through the lumen in the introducer needle to the flashback chamber or a needle hub or space between the needle and catheter. In accordance with accepted practices, if the medical personnel observe such blood flashback in the flashback chamber it is concluded that the open end of the tubular member also resides in the blood vessel. It should be noted that if the medical personnel do not observe such blood flashback, the medical personnel again attempt to insert the needle into the target vein and/or identify a new target vein and repeat to the extent necessary any of the foregoing steps (e.g., repeat the process if the new target vein is in another location or body part).

If it is determined that the needle end 22 is in the blood vessel/vein, the medical personnel then take the appropriate actions to remove the introducer needle 20 from the in-line IV catheter 10d. Typically, the medical personnel would grasp a handle, the flashback chamber or other mechanism of the related structure of the introducer needle 20 and draw the needle in a proximal direction thereby drawing the sharp end of the needle through and thence out of the in-line IV catheter. After the introducer needle 20 is removed from the in-line valve IV catheter 10d, the catheter remains positioned in the blood vessel (i.e., the open end thereof is within the blood vessel). It should be noted that after such removal or in conjunction with such removal, a needle end protection device can be actuated to protect users from the needle's sharp end 22, thereby preventing accidental needle sticks, such as, for example, the safety shield devices described in PCT Publication No. WO 2005/042073 published May 12, 2005. In addition, the medical personnel can advance the in-line valve IV catheter 10d deeper into the vein by pushing gently on the coupling end 110 of the proximal housing 100 as the catheter is being advanced off the introducer needle 20 to arrive at the orientation shown in FIG. 15B.

At this point, the in-line valve IV catheter 10d is now positioned within the vein as a completely enclosed direct luer vascular access system ready to receive a luer end such as for a syringe or an IV tubing system. The in-line valve IV catheter 10d of the present invention thus allows immediate luer access to the blood vessel of the patient for infusion of medication or blood collection utilizing a blood collector having a luer tip as are known in the art.

Referring now also to FIG. 15C, in which is shown an annotated cross-section view illustrating fluid flow in the distal direction; when the in-line valve IV catheter 10d is configured in the valve open configuration, fluid is free to flow from the coupling connection 110 through the channels 314g in the seal member proximal end 310, about the seal member 300 in a portion of the proximal housing inner cavity 130 and thence through the windows 340 of the seal member. The fluid continues to flow through the seal member inner cavity 302, through the aperture or opening in the locking ring member 400, through the distal chamber inner cavity 230, through the lumen in the tubular member 250 and thence into the blood vessel. The converse would apply if the fluid was to flow in the proximal direction such as in the case where fluid was being extracted from the blood vessel such as for sampling for diagnostic testing.

When the male luer is detached or decoupled from the coupling connection 110 of the proximal housing 100, the axial force displacing the sealing portion 330 of the seal member is no longer being applied to the seal member proximal end 310. As herein described, when the axial force is removed, the resiliency of the seal member 300 causes the proximal portion 310 thereof to move proximally and axially so as to cause the sealing portion 330 to again sealingly engage the seating surface 114 of the proximal housing. Thus, the in-line valve IV catheter 10d is restored or returned to the valve closed condition.

When the in-line valve IV catheter 10d is no longer needed, the medical personnel, using appropriate techniques, would remove the tubular member 250 from the blood vessel and tissues of the patient.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. An in-line valve IV catheter device comprising:
a housing defining a chamber;
a tubular member extending distally from the housing and defining a lumen therein that is fluidly coupled to the chamber;
a seal member disposed within the chamber and being movable between a first position sealingly engaged to a region of the housing and a second position to permit fluid flow through the housing, and wherein the seal member includes a septum configured to removably receive an introducer needle; and
a compression member coupled to the seal member at least partially about the septum, the compression member being configured and dimensioned to apply an inwardly directed force to assist re-sealing of the septum during and after withdrawal of the introducer needle from the septum.

2. The in-line valve IV catheter device of claim 1, further comprising a locking member positioned to retain the seal member within a proximal portion of the housing such that the seal member is sealingly and compressibly retained between a proximal end of the chamber and the locking member.

3. The in-line valve IV catheter device of claim 1, wherein the seal member includes at least one through-aperture extending between an inner cavity of the seal member and an outside surface of the seal member and the seal member is arranged in a proximal portion of the housing so that the seal member inner cavity is fluidly coupled to a portion of the chamber disposed in a distal portion of the housing.

4. The in-line valve IV catheter device of claim 3, wherein the seal member further includes a proximal end, a portion of the proximal end of the seal member having a sealing portion for sealing engagement with at least the proximal portion of the housing when the seal member is in the first position, and wherein the proximal portion of the housing further includes an opening that is fluidly coupled to a proximal end of the chamber, the opening being selectively fluidly coupled to the seal member inner cavity by moving the seal member to the second position, wherein the sealing portion is out of engagement with the proximal portion of the housing.

5. The in-line valve IV catheter device of claim 1, wherein the compression member is rigid.

6. The in-line valve IV catheter device of claim 1, wherein the compression member has an inner diameter smaller than an outer diameter of the septum.

7. The in-line valve IV catheter device of claim 1, wherein the compression member has at least one friction element on an inner diameter thereof.

8. The in-line valve IV catheter device of claim 1, wherein the compression member has a stop on one end for facilitating placement of the compression member on the septum.

9. A vascular access device comprising:
a housing including a housing proximal portion and a housing distal portion which define a chamber therein, the housing proximal portion having a distal reduced-diameter portion and a widened portion, the chamber having a proximal end positioned at a junction of the reduced-diameter portion and the widened portion;
a seal member movable from a first position to a second position, the seal member having a septum and a sealing portion and being disposed within the chamber to sealingly engage with at least a portion of the junction in the first position and permit fluid flow through the housing in the second position;
a compression member positioned at least partially about the septum and being configured and dimensioned to apply an inwardly directed force to apply pressure to the septum; and
an object that is arranged to pass through the septum.

10. The vascular access device as recited in claim 9, wherein the compression member surrounds and radially compresses the septum.

11. The vascular access device as recited in claim 9, wherein the compression member is a slotted ring.

12. The vascular access device as recited in claim 9, wherein the compression member has two opposing flat sides interconnected by semi-circular sections such that the opposing flat sides apply compression to the septum.

13. The vascular access device as recited in claim 12, wherein the septum defines an elongated slit having a height substantially parallel to the two opposing flat sides.

14. The vascular access device as recited in claim 9, wherein the compression member is a substantially circular asymmetrical ring with a substantially flattened portion.

15. The vascular access device as recited in claim 9, wherein the compression member is a crimped ring.

16. The vascular access device as recited in claim 9, wherein the compression member has at least one rigid arcuate section retained against the septum by an elastic band.

17. The vascular access device as recited in claim 9, wherein the compression member is a split ring having end portions that overlap and protrude such that upon movement of the end portions, a diameter of the split ring increases.

18. The vascular access device as recited in claim 9, wherein the compression member is a U-shaped member, wherein upon placement of the compression member about the septum, each end of the U-shaped member is formed tightly around the septum.

19. The vascular access device as recited in claim 9, wherein the compression member is a U-shaped clip.

20. An in-line IV catheter device comprising:
   a housing defining a chamber having a proximal portion and a distal portion;
   an elongated cannula removably extending through the housing and defining an axis;
   a seal member positioned within the proximal portion of the chamber for sealing engagement with housing and, thereby, preventing fluid flow through the in-line valve IV catheter device, the seal member having sidewalls that extend along the axis and defining a proximal cavity and a septum, wherein the elongated cannula can be selectively passed through the septum; and
   a compression member at least partially surrounding the septum, the compression member being configured and dimensioned to apply an inwardly directed force to the septum such that the septum seals when the elongated cannula is removed;
   wherein when fluid flow in either direction through the in-line valve IV device is desired, the seal member can be selectively displaced from the proximal portion of the chamber to establish an open fluid flow path within the housing.

21. The in-line IV catheter device as recited in claim 20, wherein the seal member is constructed of a generally resilient material.

22. The in-line LV catheter device as recited in claim 20, wherein the seal member includes at least one raised section extending proximally from the sidewalls to form at least one channel fluidly coupled with the chamber.

23. The in-line IV catheter device as recited in claim 22, wherein the seal member includes a sealing portion, the sealing portion being positioned within the proximal portion of the chamber such that when the sealing portion of the seal member is displaced from the proximal portion of the chamber, at least one flow path is established via the at least one channel through the in-line valve LV catheter device.

24. The in-line IV catheter device as recited in claim 20, wherein the sidewalls are arranged so as to form a shape selected from the group consisting of cylindrical, triangular, square, pentagonal, hexagonal, septogonal, octagonal and polygonal.

25. The in-line IV catheter device as recited in claim 20, wherein the sidewalls extend distally beyond the septum so as to create a collar portion.

26. The in-line IV catheter device as recited in claim 20, further comprising a ring member for retaining the seal member within the proximal portion of the chamber in sealing engagement with the housing.

27. The in-line IV catheter device as recited in claim 26, wherein the seal member and the ring member combine to operate as a valve.

28. The in-line IV catheter device as recited in claim 20, wherein the septum has a preformed slit for receiving the cannula.

29. The in-line IV catheter device as recited in claim 20, wherein the compression member has an inner diameter relatively smaller than an outer diameter of the septum.

30. The in-line IV catheter device as recited in claim 29, wherein the septum has an outer diameter of approximately 0.150 inch and the compression member has an inner diameter in a range of 0.120 to 0.145 inch.

31. The in-line IV catheter device as recited in claim 20, wherein the compression member is fabricated from a material selected from the group consisting of plastic, polycarbonates, stainless steel, an elastic material, a semi-resilient material and combinations thereof.

32. An in-line valve IV catheter device comprising:
   a housing including an inner wall defining a chamber;
   a tubular member extending distally from the housing and defining a lumen therein that is fluidly coupled to the chamber;
   a seal member disposed within the chamber and including a septum configured to removably receive an introducer needle, wherein the septum is spaced from the inner walls of the housing; and
   a compression member coupled to the seal member and being positioned at least partially about the septum spaced from the inner wall of the housing, the compression member being configured and dimensioned to apply an inwardly directed force to the seal member to assist re-sealing of the septum during and after withdrawal of the introducer needle from the septum.

33. The in-line IV catheter device as recited in claim 32, wherein the seal member is movable within the housing between a first position, in which the seal member is sealingly engaged to a region of the housing, and a second position, wherein the seal member is spaced apart from the region of the housing, to permit fluid flow through the housing.

* * * * *